(12) United States Patent
Graham et al.

(10) Patent No.: US 8,915,918 B2
(45) Date of Patent: Dec. 23, 2014

(54) BONE PLATE SYSTEM FOR BONE RESTORATION AND METHODS OF USE THEREOF

(76) Inventors: Thomas James Graham, Timonium, MD (US); Louise M. Focht, Del Mar, CA (US)

( * ) Notice: Subject to any disclaimer, the term of this patent is extended or adjusted under 35 U.S.C. 154(b) by 1665 days.

(21) Appl. No.: 12/114,695

(22) Filed: May 2, 2008

(65) Prior Publication Data

US 2009/0275947 A1 Nov. 5, 2009

(51) Int. Cl.
*A61B 17/70* (2006.01)
*A61B 17/80* (2006.01)

(52) U.S. Cl.
CPC .................................. *A61B 17/8061* (2013.01)
USPC ................................................ 606/71; 606/70

(58) Field of Classification Search
USPC ....................... 606/70, 71, 280–283
See application file for complete search history.

(56) References Cited

U.S. PATENT DOCUMENTS

| | | | |
|---|---|---|---|
| 565,255 A | 8/1896 | Belden | |
| 583,455 A | 6/1897 | Bush | |
| 1,608,790 A | 11/1926 | Henslow | |
| 2,031,483 A | 2/1936 | Interrante | |
| 2,031,484 A | 2/1936 | Interrante | |
| 3,939,828 A | 2/1976 | Mohr et al. | |
| 4,409,970 A | 10/1983 | Carrel | |
| 4,658,822 A | 4/1987 | Kees, Jr. | |
| 4,838,254 A | 6/1989 | Gauthier | |
| 4,852,559 A | 8/1989 | Chernoff | |
| 5,006,120 A | 4/1991 | Carter | |
| 5,013,314 A | 5/1991 | Firica et al. | |
| 5,092,889 A | 3/1992 | Campbell, Jr. | |
| 5,312,426 A | 5/1994 | Segawa et al. | |
| 5,372,604 A | 12/1994 | Trott | |
| 5,374,268 A | 12/1994 | Sander | |
| 5,441,509 A | 8/1995 | Vidal et al. | |
| 5,487,746 A | 1/1996 | Yu et al. | |
| 5,507,747 A | 4/1996 | Yuan et al. | |
| 5,586,985 A | 12/1996 | Putnam et al. | |
| 5,709,682 A | 1/1998 | Medoff | |
| 5,718,704 A | 2/1998 | Medoff | |
| 5,827,286 A * | 10/1998 | Incavo et al. | 606/71 |
| 5,931,839 A | 8/1999 | Medoff | |
| 5,935,128 A | 8/1999 | Carter et al. | |
| 5,941,878 A | 8/1999 | Medoff | |
| 6,066,141 A | 5/2000 | Dall et al. | |
| 6,077,266 A | 6/2000 | Medoff | |
| 6,113,603 A | 9/2000 | Medoff | |
| 6,248,109 B1 | 6/2001 | Stoffella | |
| 6,302,884 B1 | 10/2001 | Wellisz et al. | |

(Continued)

*Primary Examiner* — Christian Sevilla
(74) *Attorney, Agent, or Firm* — Tarolli, Sundheim, Covell & Tummino LLP

(57) ABSTRACT

A bone plate system is provided herein. The system may include a first and a second bone plate, which plates may be affixed to one or more bone portions and each other, so as to align and stabilize the bone and correct a bone fracture. A first bone plate is provided which includes both a bone contacting and a top surface, one of which corresponds to a primary plane. The first bone plate may be configured to engage a bone portion and a secondary plate. A secondary bone plate is provided, which plate is configured to engage the first plate. The secondary plate includes a bone contacting surface, which corresponds to one or more planes or an arc that are provided at an angle or substantially perpendicular to the primary plane. Methods of using such bone plating systems for the reduction, restoration and treatment of bone fractures are provided.

28 Claims, 14 Drawing Sheets

(56) References Cited

U.S. PATENT DOCUMENTS

| | | |
|---|---|---|
| 6,302,887 B1 | 10/2001 | Spranza et al. |
| 6,440,135 B2 | 8/2002 | Orbay et al. |
| 6,464,710 B1 | 10/2002 | Foster |
| 6,554,835 B1 | 4/2003 | Lee |
| 6,652,530 B2 | 11/2003 | Ip et al. |
| 7,037,308 B2 | 5/2006 | Medoff |
| 7,090,676 B2 | 8/2006 | Huebner et al. |
| 7,189,237 B2 | 3/2007 | Huebner |
| 7,229,445 B2 * | 6/2007 | Hayeck et al. ............ 606/70 |
| 7,235,079 B2 | 6/2007 | Jensen et al. |
| 7,250,053 B2 | 7/2007 | Orbay |
| 7,316,687 B2 | 1/2008 | Aikins et al. |
| 7,326,212 B2 | 2/2008 | Huebner |
| 2002/0095157 A1 | 7/2002 | Bowman |
| 2002/0143339 A1 | 10/2002 | Medoff |
| 2002/0147452 A1 | 10/2002 | Medoff et al. |
| 2003/0114856 A1 * | 6/2003 | Nathanson et al. ......... 606/70 |
| 2004/0102778 A1 * | 5/2004 | Huebner et al. ............ 606/71 |
| 2004/0158251 A1 | 8/2004 | Morrison et al. |
| 2004/0230312 A1 | 11/2004 | Hanson et al. |
| 2005/0070902 A1 | 3/2005 | Medoff |
| 2005/0154392 A1 | 7/2005 | Medoff et al. |
| 2005/0234458 A1 | 10/2005 | Huebner |
| 2005/0245931 A1 | 11/2005 | Orbay |
| 2006/0004361 A1 * | 1/2006 | Hayeck et al. ............ 606/69 |
| 2006/0015101 A1 | 1/2006 | Warburton et al. |
| 2006/0089648 A1 | 4/2006 | Masini |
| 2006/0155284 A1 | 7/2006 | Doherty et al. |
| 2006/0173458 A1 | 8/2006 | Forstein et al. |
| 2006/0189992 A1 | 8/2006 | Medoff |
| 2006/0241612 A1 | 10/2006 | Medoff |
| 2007/0118126 A1 | 5/2007 | Medoff et al. |
| 2007/0123880 A1 | 5/2007 | Medoff |
| 2007/0173840 A1 * | 7/2007 | Huebner ............ 606/69 |
| 2007/0173841 A1 | 7/2007 | Ralph et al. |
| 2009/0043310 A1 | 2/2009 | Rasmussen |

\* cited by examiner

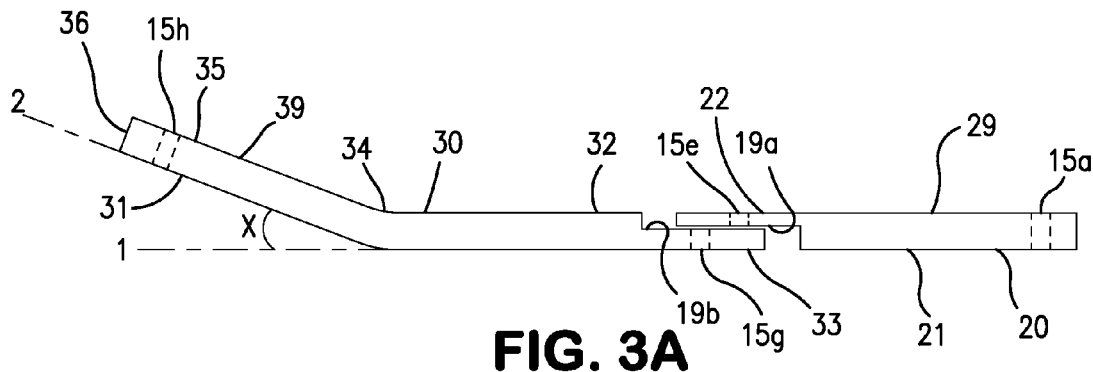
FIG. 3A
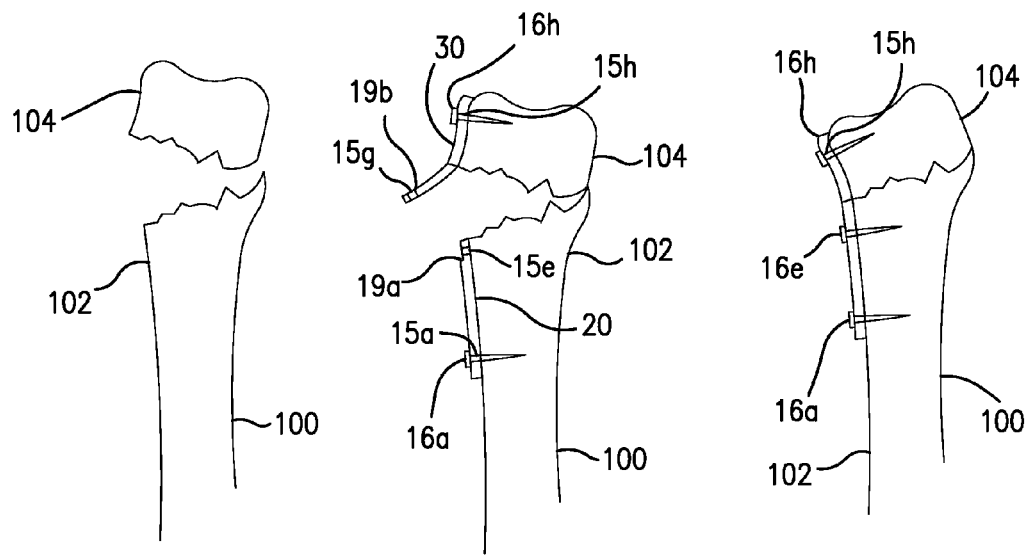
FIG. 3B  FIG. 3C  FIG. 3D

FIG. 4A  FIG. 4B

BONE PLATE SYSTEM FOR BONE RESTORATION AND METHODS OF USE THEREOF

BACKGROUND

A bone fracture is a condition of a bone in which at least a portion of the bone has cracked, broken, and/or fragmented. Bone fractures can be caused in several different ways, for instance, as a result of a high force impact, stress, or as the result of conditions that presuppose the bones for fracturing, such as osteoporosis, cancer, and the like. Fractures may be closed or compound and they may be simple or multi-fragmentary, e.g., comminuted.

The ease and success of treatment of bone fractures often depends on the type and location of the fracture and the tools available for correcting the crack, break, and/or fragmentation of the bone to be treated. For instance, a closed, simple fracture along a diaphyseal portion of a long bone may be relatively simple to correct and therefore treat. However, a distal fracture of the distal radius, e.g., a Colles' fracture, due to its location and the morphology of the bones involved, may be difficult to correct and treat.

There are several methods for treating bone fractures, all of which typically involve the stabilization of the bone fragments. For instance, the fractured bone pieces may be reduced, e.g., aligned, and restored to their natural position, which position is then maintained using standard immobilization techniques, such as using plaster or fiberglass casts, as well as implanting surgical nails, screws, plates, and wires which function to fix and hold the fractured bone together.

However, the use of casts and typical surgical nails, screws, plates, and wires for the treatment of fractured bones have several drawbacks. For example, casts are problematic in that they are big, bulky and usually only allow a small degree of motion of associated joints. Further, casts often fail to provide adequate internal fixation, thus, resulting in pain, deformity, and/or prolonged disability. Additionally, the use of typical nails, screws, plates, and wires can be problematic because these devices may be hard to apply, are not easily manipulated so as to appropriately reduce and fix the bone in correct alignment, and are not suited for reducing fragments that are displaced from the main loci of the fracture, often requiring additionally plating and/or wiring.

The details of one or more variations of the subject matter described herein are set forth in the description below and the accompanying drawings. Other features and advantages of the subject matter described herein will be apparent from the description and drawings, and from the claims.

SUMMARY

Aspects of the present disclosure include a bone plate system. The bone plate system may include at least a first and a second bone plate, which bone plates may be affixed to one or more bone portions, and/or each other, so as to align and stabilize the bone and thereby correct and/or treat a bone fracture. For instance, in certain embodiments, the bone plate system includes at least a first plate, e.g., a diaphyseal bone plate, and a second plate, e.g., a periarticular bone plate, which bone plates may be configured so as to be coupled together and/or to attach to one or more fragmented bone pieces and thereby be used to reduce and/or fix a fractured bone portion for the treatment thereof.

Specifically, in certain embodiments, the bone plate system includes a diaphyseal bone plate, which bone plate includes both a bone contacting surface and a top surface that is opposite the bone contacting surface. In certain embodiments, at least one of the bone contacting surface and the top surface corresponds to a primary plane. Further, the diaphyseal bone plate may be configured to engage one or more of a bone portion and a periarticular plate. For instance, the diaphyseal bone plate may include a plurality of openings between the bone contacting surface and the top surface. For example, the diaphyseal bone plate may include at least one opening that is configured to receive a fastener so as to attach the diaphyseal bone plate to one or more portions of bone. Additionally, the diaphyseal bone plate may further include an opening for receiving a fastener so as to attach a portion of the diaphyseal bone plate to a portion of a periarticular bone plate.

Additionally, the bone plate system includes a periarticular bone plate, which bone plate is configured to engage one or more of a diaphyseal bone plate and a bone portion. For instance, in certain embodiments, the bone plate system includes a periarticular bone plate that is configured for being coupled to the diaphyseal bone plate and/or attached to the bone. For example, the periarticular bone plate may include a first portion having an opening for receiving a fastener to attach the first portion of the periarticular bone plate to at least one of the diaphyseal bone plate and a bone portion. In certain embodiments, the periarticular bone plate may include a second portion having an opening for receiving a fastener for attaching the second portion to another portion of bone. Further, in certain embodiments, the periarticular bone plate may also include a bone contacting surface, which surface corresponds to one or more planes or an arc that are provided at an angle or substantially perpendicular to the primary plane. Methods of using such bone plating systems for the reduction and/or the restoration and/or treatment of bone fractures, for example, are also provided herein.

Further, in another aspect, the present disclosure is directed to a bone fixation element, e.g., a fastener, which bone fixation element may be used in conjunction with a bone plate system of the disclosure. A fastener of the disclosure may include an extended body. In certain variations, the extended body includes a proximal portion including a proximal end, a distal portion including a distal end, and an elongate portion extending between said proximal and distal portions. In certain variations, the proximal portion includes a shaft, wherein the shaft includes at least one smooth region and at least one threaded region, wherein the smooth region may be positioned between the proximal end and the threaded region and may include a length that corresponds to a thickness of a bone plate, e.g., a primary or extender bone plate.

BRIEF DESCRIPTION OF THE DRAWINGS

According to common practice, the various features of the drawings may not be presented to-scale. Rather, the dimensions of the various features may be arbitrarily expanded or reduced for clarity. Included in the drawings are the following figures:

FIG. 1 illustrates a bone plate system in accordance with the present disclosure.

FIG. 2 illustrates the bone plate system of FIG. 1, as the individual plates would be attached to the bone, the plates coupled together, and attached to one another.

FIG. 3 illustrates a side view of a bone plate system in accordance with the present disclosure. FIG. 3A provides a side view of a bone plate system as described herein, wherein the bone plate system includes a primary bone plate and a secondary bone plate prior to the coupling of the bone plates. FIG. 3B provides a side view of a fractured bone portion, wherein one bone portion is fractured and displaced relative to another bone portion. FIG. 3C provides a side view of the bone plate system of FIG. 3A, wherein the primary and secondary bone plates are attached to respective bone portions, prior to coupling of the bone plates. FIG. 3D provides a side view of the bone plate system of FIG. 3C, wherein the primary and secondary bone plates are attached to respective bone portions, subsequent to coupling of the bone plates.

FIG. 4 illustrates another variation of a bone plate system in accordance with the present disclosure. FIG. 4A provides a top view of a primary bone plate and a curved secondary bone plate prior to being coupled. FIG. 4B provides a bottom view of the bone plate system of FIG. 4A.

FIG. 5 illustrates another variation of a bone plate system in accordance with the present disclosure.

FIG. 6 illustrates another variation of a bone plate system in accordance with the present disclosure.

FIG. 7 illustrates another variation of a bone plate system in accordance with the present disclosure.

Like reference symbols in the various drawings indicate like elements.

DEFINITIONS

Figure 1A:
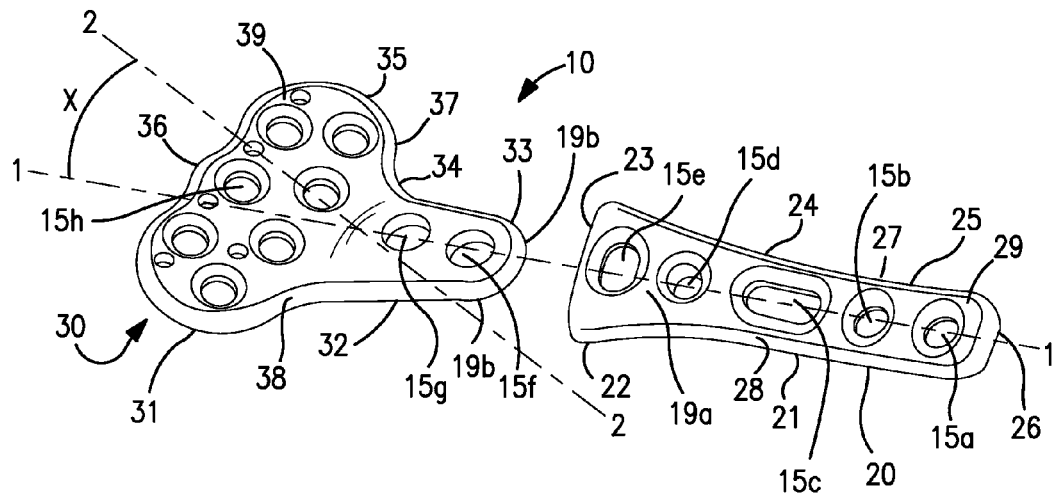
FIG. 1A provides a perspective view of a top surface of a bone plate system as described herein, wherein the bone plate system includes a primary bone plate and a secondary bone plate prior to the coupling of the bone plates.

Before the present subject matter is further described, it is to be understood that this subject matter described herein is not limited to particular embodiments described, as such may of course vary. It is also to be understood that the terminology used here in is for the purpose of describing particular embodiments only, and is not intended to be limiting. Unless defined otherwise, all technical terms used herein have the same meaning as commonly understood by one skilled in the art to which this subject matter belongs.

Where a range of values is provided, it is understood that each intervening value, to the tenth of the unit of the lower limit, unless the context clearly dictates otherwise, between the upper and lower limit of that range, and any other stated or intervening value in that stated range, is encompassed within the subject matter described herein. The upper and lower limits of these smaller ranges may independently be included in the smaller ranges, and are also encompassed within the subject matter described herein, subject to any specifically excluded limit in the stated range. Where the stated range includes one or both of the limits, ranges excluding either or both of those included limits are also included in the subject matter described herein.

It must be noted that as used herein and in the appended claims, the singular forms "a", "and", and "the" include plural referents unless the context clearly dictates otherwise. Thus, for example, reference to a "fastener" includes a plurality of such fasteners, and reference to "the engagement element" includes reference to one or more engagement elements and equivalents thereof known to those skilled in the art, and so forth.

It is further noted that the claims may be drafted to exclude any optional element. As such, this statement is intended to serve as antecedent basis for use of such exclusive terminology as "solely", "only" and the like, in connection with the recitation of claim elements, or the use of a "negative" limitation. Accordingly, the term "optional" or "optionally present"—as in an "optional element" or an "optionally present element" means that the subsequently described element may or may not be present, so that the description includes instances where the element is present and instances where it is not.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

DETAILED DESCRIPTION

Aspects of the subject matter described herein include a bone plate system. The bone plate system may include at least a first and a second bone plate, which bone plates may be affixed to one or more bone portions and/or each other, so as to align and stabilize the bone and thereby correct and/or treat a bone fracture. It is to be noted that reference to "a bone" and/or "a bone portion" are not limited to a single bone and/or a single bone portion, but rather one or more bones or one or more bone portions pertaining to one or more separate bones may be referred to thereby. Accordingly, in certain embodiments, the bone plate system includes at least a primary bone plate, sometimes referred to herein as a proximal or diaphyseal bone plate, and a secondary bone plate, sometimes referred to herein as a distal, periarticular, or juxta-articular bone plate, dependent upon its intended position on the bone, which bone plates may be configured so as to be coupled together and/or to attach to one or more fragmented bone pieces and thereby be used to reduce and/or fix a fractured bone portion for the treatment thereof.

Specifically, in certain embodiments, the bone plate system includes a first bone plate, which first bone plate may be a proximal or diaphyseal bone plate. The diaphyseal bone plate may include both a bone contacting surface and a top surface that is opposite the bone contacting surface. In certain embodiments, at least one of the bone contacting surface and the top surface corresponds to a primary plane. Further, in certain embodiments, the primary or diaphyseal bone plate may be configured to engage one or more of a bone portion and a secondary bone plate. For instance, in certain embodiments, the diaphyseal bone plate may include a plurality of openings between the bone contacting surface and the top surface. For example, the diaphyseal bone plate may include at least one opening that is configured to receive a fastener so as to attach the diaphyseal bone plate to one or more portions of bone. Additionally, the diaphyseal bone plate may further include an opening for receiving a fastener so as to attach a portion of the diaphyseal bone plate to a portion of the secondary bone plate.

Additionally, in certain embodiments, the bone plate system includes a second bone plate, which bone plate may be a distal, periarticular, or juxta-articular bone plate. The secondary, bone plate is configured to engage one or more of a primary, e.g., diaphyseal, bone plate and a bone portion. For instance, in certain embodiments, the bone plate system includes a periarticular or juxta-articular bone plate that is configured for being coupled to the diaphyseal bone plate and/or attached to a bone portion. For example, in certain embodiments, the periarticular r bone plate includes a first portion having an opening for receiving a fastener to attach the first portion of the periarticular r bone plate to at least one of the diaphyseal bone plate and the bone. In certain embodiments, the periarticular bone plate includes a second portion having an opening for receiving a fastener for attaching the second portion to a second portion of bone. Further, in certain embodiments, periarticular bone plate may also include a bone contacting surface, which surface corresponds to one or more planes or an arc that are provided at an angle or substantially perpendicular to the primary plane. Methods of using such bone plating systems for the reduction and/or the restoration and/or treatment of bone fractures, for example, are also provided herein.

Embodiments of the subject bone plating system will be described first, followed by a description of the use thereof, e.g., for the reduction and/or fixation of bone portions for the restoration and/or treatment of bone fractures.

As summarized above, some of the embodiments provide for a bone plate system. In certain embodiments, the bone plate system may be employed to reduce and/or fix one or more bone portions for the treatment of a bone fracture, for example. The bone plate system includes a plurality of bone plates, for instance, a first or primary bone plate, e.g., a diaphyseal bone plate, and a second or secondary bone plate, e.g., a periarticular bone plate, which bone plates may be configured for being attached to one or more bone portions and may be adapted to be coupled together with one another so as to reduce, fix and/or stabilize, for example, the one or more bone portions in healing alignment for the treatment of a bone fracture.

In certain embodiments, the first and second bone plates are configured such that at least one surface thereof is at an angle to another surface thereof. For instance, one or more surfaces may include a curvature or angle such that a plane of the surface is angled with respect to a plane of another surface. In certain embodiments, the first and second bone plates are configured such that when coupled, one or more surfaces thereof are at an angle to each other. For instance, in certain embodiments, the bone plate system includes an engagement element configured for allowing a first or primary bone plate, e.g., a diaphyseal bone plate, to be coupled to a second or secondary bone plate, e.g., a periarticular bone plate at an angle to one another. Accordingly, the diaphyseal and periarticular bone plates, as well as the engagement element, may have a variety of configurations ranging from planar to non-planar in relationship to one another. At least in this manner, the bone plate system may be readily adaptable to bone portions of varying morphologies so as to aid in the reduction and/or realignment of bone fractures.

Due to the adaptability of the bone plate system to differing bone morphologies, the system is well suited for reducing and fixing comminuted fractures, wherein the fracture includes a fragmented bone portion that is distal to the loci of a primary bone shaft portion and/or positioned at an angle thereto. For example, the present bone plate system may be configured so as to reduce and align fragmented bone portions wherein the fragmented bone portions are both distanced and out of plane from one another.

A bone plate and/or suitable fastener of the subject bone plate system may be fabricated from any suitable biocompatible material so long as the plates are of sturdy yet malleable construction. For instance, in certain embodiments, a bone plate may be fabricated from a suitable metal material containing a metal such as stainless steel, titanium, cobalt chromium, and/or an alloy thereof. Further, suitable materials may be a bioabsorbable material such as polygalactic acid (PGA), polylactic acid (PLA), copolymers thereof, and the like. Other suitable materials include plastic, ceramics, and the like. In general, one or more of the bone plates may be fabricated from a suitable material so as to be stiffer and stronger than the section of bone spanned by the plate(s), yet flexible enough not to significantly strain the bone. In certain embodiments, a bone plate may be fabricated in accordance with such well known methods as stamping, machining, casting, laser cutting, molding, and the like.

In certain embodiments, the bone plate system may be configured such that a primary bone plate may be attached to a diaphyseal bone portion and positioned along a primary plane pertaining thereto, thus the primary bone plate may be referred to as a diaphyseal bone plate; and a secondary bone plate may be attached to a metaphyseal or epiphyseal bone portion and positioned along a secondary plane pertaining thereto, thus the secondary bone plate may be referred to as a periarticular or juxta-articular bone plate, wherein the two bone portions are out of plane from one another, e.g., primary and secondary planes pertaining to a top or bottom surface of the two bone plates are anti-parallel to one another.

In such an instance, the configuration(s) of the primary, e.g., diaphyseal, and secondary, e.g., periarticular, bone plates, as well as the engagement element there between, is such that the two bone plates may be coupled with one another so as to correctly reduce, align, stabilize, and/or restore the two bone portions to a position that at least approximates their natural position and thereby treats the bone fracture. Accordingly, given the adaptable configurations of the various elements of the bone plate system, the present system is capable of reducing and fixing a bone fracture, such as a fracture of the radius or ulna bones. Specifically, a primary bone plate may be attached to a first bone portion, such as a radial bone portion that is proximal to a fracture site, and a secondary bone plate may be attached to a second bone portion, such as a radial bone portion that is distal to a fracture site, and the two bone plates may be coupled to one another so as to align the two bone portions and reduce the fracture there between.

Accordingly, a subject bone plate system may have a variety of configurations adapted to capture fracture fragments, which are distanced from a primary bone portion, and reduce the fragmented portion(s) in correct alignment with the primary bone portion so as to stabilize the fracture portions and facilitate the appropriate healing of the fractured and/or fragmented bone. To that extent, the bone plates of the present bone plate system may include a multiplicity of elements, for instance, engagement elements (which may include tab and tab receiving portions of varying angles), as well as openings (such as apertures of differing configurations that are adapted to receive and align a fastener at varying orientations to the bone plate and/or underlying bone). In this manner, the bone plate system provides a flexible interface for reducing and stabilizing fractures, including periarticular or juxta-articular fractures that are out of plane from a main, primary bone shaft.

Hence, in some embodiments, due in part to the configuration of the primary and secondary bone plates themselves, the configuration of the engagement element portion between the plates, which may include an angled configuration, and/or due in part to the position and configuration of the openings within the plates, the subject bone plate system may be adapted to be attached to a wide range of bone positions, including along a radial bone shaft and/or along a radial platform, and/or along an internal or external surface of the radial bone shaft, so as to stabilize and reduce a bone fracture there between.

For instance, where a fracture includes a dorsally-displaced distal radius fracture, a primary bone plate of the system, e.g., a diaphyseal bone plate, containing a contoured tab receiving portion, may be positioned centrally along a volar surface of the diaphyseal bone portion proximal to a fracture of the radius bone. In such an embodiment, a secondary bone plate of the system, e.g., a periarticular or juxta-articular bone plate, containing an angled tab insertion portion, may be positioned along a volar surface of the fractured and/or displaced distal radius portion distal to the site of the fracture, and the two plates may be coupled so as to align the two bone portions together and thereby reduce the fracture.

Accordingly, where the tab portion recapitulates a desired angle of the volar radius, the coupling of the secondary bone plate angled tab insertion portion into the contoured tab receiving portion of the primary bone plate results in the establishment of a natural reduction of the radius fracture. Further, where the tab receiving portion of the primary bone plate includes an opened or widened contour, slight radio-ulnar motion between the two plates may be allowed, thereby adding to the flexibility of the system. Additionally, to optimize bone plate alignment, the number, position, and configuration of the openings of the plates may further add to the flexibility of the system by allowing relative movement of the plates until a desired orientation has been achieved and the plates locked into position relative to each other. It is to be understood that although the above has been explained with reference to a dorsally-displaced fracture, the system is readily adaptable so as to align, reduce, and/or fix any fracture, for instance, a volarly-displaced fractured portion, such as where the bone plates are attached to respective dorsal surfaces so as to reduce the fracture.

As summarized above, in certain embodiments, the subject bone plate system includes a first bone plate (sometimes referred to herein as a primary or proximal bone plate). A primary bone plate of the subject bone plate system may have any suitable shape and have any suitable size so long as the primary bone plate is capable of being attached to a bone portion and coupled to a secondary bone plate so as to assist in the reduction and/or stabilization of one or more bone portions and thereby treat a bone fracture.

For instance, in certain embodiments, a primary bone plate may be an elongate plate member that includes a proximal portion with a proximal end, a distal portion with a distal end, and an intercalating portion between the proximal and distal portions. Specifically, the first and second ends are separated from one another, which separation defines a length of the subject plate. In certain embodiments, and dependent on the context, a distal portion of a bone plate of the subject bone plate system, refers to a region of the bone plate that contains a portion that is configured for being attached to a bone portion, where as a proximal portion of the bone plate refers to a region of the bone plate that contains a portion that is configured for being coupled to another bone plate and/or attached to a second portion of bone.

Additionally, the primary bone plate includes a top and a bottom surface, wherein the top and bottom surface are separated from one another, the separation of which defines a thickness. In certain embodiments, the primary bone plate includes a bottom surface that is configured for contacting a bone surface and therefore may be referenced as a bone contacting surface. Likewise, in certain embodiments, the primary bone plate includes a top surface that is opposite the bone contacting surface. Further, the primary bone plate includes a first side and a second side which sides are separated from each other by a distance, which distance defines a width.

In certain embodiments, the primary bone plate may have a length that ranges from about 5 mm or less to about 50 mm or more, such as about 10 mm to about 40 mm, for instance, between about 15 mm to about 30 mm, such as between about 20 mm to about 25 mm. In certain embodiments, the primary bone plate may have a thickness that may range from about 0.01 mm or less to about 4 mm or more, for instance, between about 0.1 mm to about 3 mm, such as between about 0.5 mm or about 1 mm to about 2 or about 2.5 mm. In certain embodiments, a suitable primary bone plate of the subject disclosure may have a width that ranges from about 2 mm to about 10 mm or more, for instance, between about 3 mm to about 8 mm, such as between about 4 or about 5 mm to about 6 mm or about 7 mm.

In certain embodiments, the primary bone plate is planar, wherein the proximal and distal ends define a primary plane. Accordingly, at least one of the primary bone plate bone contacting surface and the primary bone plate top surface may substantially correspond to a primary plane, wherein the primary plane is linear or otherwise flat. In certain embodiments, the primary bone plate may be angled or curved, as described below.

In some embodiments, the primary bone plate is configured for being associated with and/or attached to a bone portion, e.g., a first bone portion, such as shaft portion of a long bone. For instance, in certain embodiments, the primary bone plate is configured for being attached to a diaphyseal portion of a bone, and therefore, the primary bone plate may be referenced herein as a diaphyseal bone plate. Hence, the primary bone plate, e.g., a diaphyseal bone plate, may be configured so as to be complimentary to a bone morphology, such as the long bone morphology of a diaphyseal bone. In certain embodiments, the primary bone plate has a configuration that is complimentary to a planar portion of a bone portion, e.g., a diaphyseal bone portion, and in certain embodiments, the primary bone plate has a configuration that is complimentary to a non-planar portion of a bone portion.

Accordingly, in certain embodiments, the primary bone plate is non-planar. For instance, the primary bone plate may have a configuration that is adapted to conform to a specific bone morphology, such as a configuration that is adapted to specifically and snugly fit the bone morphology to which the bone plate is to be associated and/or attached. Hence, in certain embodiments, the primary bone plate includes an internal angled and/or arced portion between the proximal and distal ends thereof and is therefore angled and/or arced in correspondence to a bone surface to which the plate is to be associated.

For example, in certain embodiments, the bone contacting surface between the proximal and distal ends of the primary bone plate may include an internal angled portion, wherein the angle may range from about 1° to about 90°, such as from about 50 to about 45°, for instance from about 7.5° to about 30°, including from about 10° to about 20°, such about as 15°. In certain embodiments, the bone contacting surface between the proximal and distal ends of the primary bone plate may include an internal arced portion, wherein the arc includes a radius of curvature that ranges from about 1 mm to about 50 mm, for instance, from about 5 mm to about 30 mm, including from about 10 mm to about 20 mm, such about as 15 mm.

Further, in certain embodiments, the primary bone plate includes a curved portion between the first and second sides thereof and is therefore curved relative to a central, longitudinal axis defined by the proximal and distal ends of the primary bone plate. For instance, in certain embodiments, the primary bone plate may include an internal concave portion between the first and second sides of the bone plate. The concaved portion may run along a partial or entire length of the primary bone plate, wherein the curvature comprises a degree of curvature, e.g., a concavity, that ranges from about 5 mm to about 25 mm, such as from 1 bout 8 mm to about 20 mm, including about 10 mm to about 15 mm.

In certain embodiments, the proximal portion of the primary bone plate, e.g., the portion adapted to be associated with a first bone portion, may include a concave configuration, e.g., a recessed portion between the sides of the bone plate that is adapted to fit around a convex bone portion, further, the distal portion, e.g., the portion adapted to be associated with a secondary bone plate, may be concave as well, substantially planar, and/or may be angled with respect to the proximal portion. For instance, the distal portion of the primary bone plate, e.g., the portion adapted to be associated with a second bone portion and/or a secondary bone plate, may include a concave configuration.

The primary bone plate may be configured for engaging or being associated with an additional bone plate and/or affixed or otherwise associated with a bone portion, e.g., a second bone portion. For instance, the proximal portion of the primary bone plate may be configured for engaging or otherwise being associated with a portion of bone, e.g., a first bone portion, and the distal portion may be configured for being associated with an additional bone plate and/or another portion of bone, e.g., a second bone portion. Specifically, the distal portion of the primary bone plate may include a bone plate engagement element, such as a periarticular bone plate engagement element, e.g., where the secondary bone plate is a periarticular bone plate.

A bone plate engagement element of the primary bone plate may have any suitable configuration so long as it is capable of facilitating an association and/or coupling of the primary bone plate with an additional plate. For instance, the bone plate engagement element of the primary bone plate may be a configuration that is adapted to allow the primary bone plate to be associated with a secondary bone plate. Hence, the bone plate engagement element may include a recess, groove, flattened, hooded, or slot-like configuration that is positioned at a distal portion of the primary bone plate and adapted to receive a corresponding engagement portion of a secondary bone plate and thereby be mated therewith.

For example, where a secondary bone plate includes an bone plate engagement element (e.g., a primary bone plate engagement element) configured as an extended male insertion portion (e.g., a tab insertion portion), the primary bone plate may include a hooded slot or recessed engagement portion (e.g., a secondary bone plate engagement element) that is configured as a female tab receiving portion that is adapted to receive the insertion portion of the secondary bone plate. The hooded and recessed portion may further include a groove-like configuration in to which the insertion portion slides. The primary bone plate engagement element may also be configured as an open slot into which a corresponding bone plate tab engagement portion of the secondary bone plate may be inserted.

Accordingly, in certain embodiments, the bone plate engagement element of the primary bone plate is configured as a receptacle or tab receiving portion, wherein the receiving portion has a first width that ranges from about 2 mm to about 20 mm, for instance, between about 5 mm to about 15 mm, such as between about 7 mm and about 10 mm. In certain embodiments, the receiving portion has a second width that ranges from about 1 mm to about 18 mm, for instance, between about 3 mm to about 14 mm, such as between about 5 mm and about 7 mm or about 8 mm or about 10 mm. Accordingly, in certain embodiments, the first and second widths are distanced from one another such that the receptacle or tab receiving portion tapers along its length. In certain embodiments, the engagement element may have a length that ranges from about 5 mm to about 30 mm, for instance, between about 7.5 mm to about 25 mm, such as between about 10 mm to about 15 mm or about 20 mm. In certain embodiments, the engagement element may have a thickness that ranges from about 0.1 mm to about 3 mm, for instance, between about 0.25 mm to about 2 mm, such as between about 0.5 mm or 1 mm to about 1.5 mm.

In certain embodiments, the bone plate engagement element positioned at the distal portion of the primary bone plate, and in some embodiments the distal portion itself, is angled with respect to the proximal portion and/or proximal end of the primary bone plate. For instance, a plane defined by a top surface of the distal portion of a primary bone plate body may be angled with respect to the a plane defined by a top surface of the proximal portion of the primary bone plate such that an engagement element positioned at the distal portion of the primary bone plate is angled with respect to the distal portion of the primary bone plate. In certain embodiments, the angle between the planes defined by the two surfaces may range from about 1° to about 90°, such as from about 5° to about 45°, for instance from about 7.5° to about 30°, including from about 10° to about 20°, such about as 15°. In certain embodiments, the bone plate engagement element positioned at the distal portion of the primary bone plate is not angled but rather is planar with respect to the distal end of the primary bone plate. In certain embodiments, the bone plate engagement element is a slot that is hooded and formed to be coextensive with the top or bottom surfaces of the primary bone plate. The engagement element may additionally include an orifice into which the tab portion of a secondary bone plate is inserted.

In certain embodiments, the distal region and/or bone plate engagement element of the primary bone plate includes one or more openings, such as an opening that spans the thickness of the primary bone plate and extends between a bone contacting surface and a top surface thereof. For instance, in certain embodiments, the engagement element of the primary bone plate is configured as, or includes, an opening positioned in the distal portion of the plate that is adapted for receiving a fastener, such as a fastener that may be inserted through the opening and functions to couple the primary bone plate to one or more of an additional plate or a bone portion, e.g., a second bone portion.

This opening, as well as any other opening included in the bone plate system, may be of any suitable configuration, for instance, the opening may be round, e.g., circular or semi-circular, triangular, square, ovoid, arced, elliptical, or the like. For example, in certain embodiments, the opening is circular and in certain embodiments the opening is semi-circular, arced, or ovoid. In certain embodiments, two or more openings are included and positioned at the proximal portion of the primary bone plate. For instance, in certain embodiments, one or more openings are circular and an additional one or more openings is semi-circular or arced or ovoid. Where an opening is circular, it may have a diameter that ranges from about 0.5 mm to about 5 mm, such as from about 1 mm to about 4 mm, including about 2 mm or about 2.5 mm to about 3 mm. Where an opening is ovoid, it may have a width that ranges from about 0.5 mm to about 5 mm, such as from about 1 mm to about 4 mm, including about 2 mm or about 2.5 mm to about 3 mm; and it may have a length that ranges from about 2 mm to about 15 mm, such as from about 5 mm to about 9 or about 10 mm, including about 7 mm to about 8 mm.

In certain embodiments, an intercalating or distal portion of the primary bone plate is configured for being attached to a bone portion. Hence, in certain embodiments, the primary bone plate includes one or more openings, which openings are adapted so as to receive a fastener so as to attach the bone plate to a bone portion. Accordingly, in certain embodiments, the primary bone plate includes one or more, e.g., a plurality of openings, the configurations and dimensions of which are equivalent to those described above, wherein the openings are positioned in an intercalating and/or distal portion of the primary bone plate.

For instance, in certain embodiments, the proximal body portion of the primary bone plate may include an opening that is configured for receiving a fastener, such as a fastener that is adapted so as to attach the primary bone plate to a bone portion, e.g., a first bone portion. In certain embodiments, one or more openings, as described herein, include threading such as threading that corresponds to threading positioned on a fastener. In this manner, a fastener may be inserted into and through the opening by rotating the fastener in such a manner that the threads of the fastener align with the corresponding threads of the opening. In certain embodiments, one or more openings do not include threading such that the fastener may be inserted there through without threading the fastener into the opening.

The subject bone plate system additionally includes a second bone plate (sometimes referred to herein as a secondary bone plate). A secondary bone plate of the subject plate system may have any suitable shape and have any suitable size so long as the secondary bone plate is capable of being coupled to a primary bone plate and/or associated with a bone portion, e.g., a second and/or third bone portion, so as to assist in the reduction and/or stabilization of one or more bone portions and thereby treat a bone fracture.

For instance, in certain embodiments, a secondary bone plate may be an extended or elongate plate member that includes a proximal portion with a proximal end, a distal portion with a distal end, and an intercalating portion between the proximal and distal portions. Specifically, the first and second ends are separated from one another, which separation defines a length of the subject plate. In certain embodiments, and dependent on the context, a proximal portion of the bone plate refers to a region of the secondary bone plate that contains a portion that is configured for being coupled to another bone plate and/or attached to a portion of bone, e.g., a second bone portion, whereas a distal portion of a secondary bone plate of the subject bone plate system, refers to a region of the bone plate that contains a portion that is configured for being contacted and/or attached to a bone portion, e.g., a third bone portion.

Additionally, the secondary bone plate includes a top and a bottom surface, wherein the top and bottom surface are separated from one another, the separation of which defines a thickness. In certain embodiments, the secondary bone plate includes a bottom surface that is configured for contacting a bone surface and therefore may be referenced as a bone contacting surface. Likewise, in certain embodiments, the secondary bone plate includes a top surface that is opposite the bone contacting surface. Further, the secondary bone plate includes at least a first side and a second side which sides are separated from each other by a distance, which distance defines a width.

In certain embodiments, the secondary bone plate may have a length that ranges from about 2 mm or less to about 50 mm or more, such as about 5 mm to about 25 mm, for instance, between about 8 mm to about 20 mm, such as between about 10 mm to about 15 mm. In certain embodiments, the secondary bone plate may have a thickness that may range from about 0.01 mm or less to about 3 mm or more, for instance, between about 0.1 mm to about 2.5 mm, such as between about 0.5 mm or about 1 mm to about 2.0 mm. In certain embodiments, a suitable secondary bone plate of the subject disclosure may have a width that ranges from about 2 mm or less to about 20 mm or more, for instance, between about 3 mm to about 18 mm, such as between about 5 or about 8 mm to about 12 mm or about 15 mm, for instance, about 9 mm to about 10 mm.

The secondary bone plate is configured for being associated with, e.g., contacted with and/or attached to, another bone plate, such as a primary bone plate, and/or a bone portion, e.g., a second bone portion. Additionally, in some embodiments, the secondary bone plate is configured for being associated with, e.g., contacted with and/or attached to, another bone portion, such as a third bone portion.

Accordingly, in certain embodiments, the secondary bone plate includes a proximal portion, wherein the proximal portion includes a primary bone plate engagement element, such as a tab insertion portion, that is configured for being associated with a primary bone plate. For instance, the proximal portion may include a tab insertion portion that is configured for being inserted or otherwise associated with a tab receiving portion, e.g., a slotted, grooved, or hooded tab receiving portion, of a primary bone plate. Further, in certain embodiments, the secondary bone plate includes a distal portion, which distal portion may be configured for being associated with a bone portion and to that extent may include a configuration adapted to a particular bone morphology and/or an opening, which opening is configured for facilitating the attachment of the distal portion of the secondary bone plate to a bone portion, e.g., via a fastener inserted there through.

Hence, in certain embodiments, a proximal portion of the secondary bone plate may be configured for engaging or being associated with an additional bone plate and/or affixed or otherwise associated with a bone portion, e.g., a second bone portion, whereas the distal portion of the secondary bone plate may be configured for contacting and/or otherwise engaging a bone portion, e.g., a third bone portion. For instance, the proximal portion of the secondary bone plate may be configured for being associated with a primary bone plate and/or a portion of bone, and a distal portion of the secondary bone plate may be configured for engaging or otherwise being associated with an additional portion of bone. Specifically, in certain embodiments, the proximal portion of the secondary bone plate may include a plate engagement element, such as a primary bone plate engagement element.

A bone plate engagement element of the secondary bone plate may have any suitable configuration so long as it is capable of facilitating an association and/or coupling of the secondary bone plate with a primary bone plate. For instance, the engagement element of the secondary bone plate may be a configuration that is adapted to allow the secondary bone plate to be associated with a first plate, e.g., a primary bone plate. Hence, the engagement element may include an extended portion that is configured for being inserted or otherwise associated with a groove or slot-like configuration of a primary bone plate, as described above, wherein the engagement portion is positioned at a proximal portion of the secondary bone plate and is adapted to be coupled to a corresponding engagement portion of a primary bone plate and thereby be mated therewith.

For example, where a primary bone plate includes an engagement element (e.g., a primary bone plate engagement element) configured as a female receiving portion (e.g., a tab insertion receiving portion), the secondary bone plate may include an extended engagement portion (e.g., a secondary bone plate engagement element) that is configured as an insertion member that is adapted to be received within the receiving portion of the primary bone plate.

Accordingly, in certain embodiments, the engagement element of the secondary bone plate is configured as a tab insertion portion, wherein the tab insertion portion has a first width that ranges from about 1 mm or slightly less than 2 mm to about 18 mm or slightly less than 20 mm, for instance, between about 3 mm or slightly less than 5 mm, to about 14 mm or slightly less than 15 mm, such as between about slightly less than 7 mm to about slightly less than 10 mm. In certain embodiments, the tab insertion portion has a second width that ranges from about 1 mm to about slightly less than 18 mm, for instance, between about 3 mm or slightly less than 4 mm to about slightly less than 14 mm, such as between about 5 mm and about slightly less than about 7 mm or about 8 mm or about slightly less than 10 mm. Accordingly, in certain embodiments, the first and second widths are distanced from one another such that the tab insertion portion tapers along its length. In certain embodiments, the tab insertion portion may have a length that ranges from about 2 mm to about slightly less than 30 mm, for instance, between about 5 mm or slightly less than 6 mm to about slightly less than 25 mm, such as between about slightly less than 10 mm to about slightly less than about 15 mm or about 20 mm. In certain embodiments, the engagement element may have a thickness that ranges from about 0.1 mm to about 3 mm, for instance, between about 0.25 mm to about 2 mm, such as between about 0.5 mm or 1 mm to about 1.5 mm.

It is to be noted that with respect to the above descriptions, the primary bone plate is described as including a female receiving engagement element, and the secondary bone plate is described as including a male insertion engagement element. Nevertheless, in certain embodiments, the primary bone plate includes a male insertion engagement element, as that element is described above with respect to the secondary bone plate, and the secondary bone plate includes a female receiving engagement element, as that element is described above with respect to the primary bone plate.

In certain embodiments, the bone plate engagement element is positioned at the proximal portion of the secondary bone plate, and in some cases the proximal portion itself, is angled with respect to a distal portion and/or distal end of the secondary bone plate. For instance, a plane defined by a top surface of the proximal portion of the secondary bone plate body may be angled with respect to a plane defined by a top surface of the distal portion of the secondary bone plate body such that an engagement element positioned at the proximal portion of the secondary bone plate is angled with respect to the distal portion of the secondary bone plate.

Accordingly, in certain embodiments, the proximal portion containing the engagement element of the secondary bone plate may be angled with respect to the distal portion. For instance, in certain embodiments, there is an angle between the engagement element portion of the proximal portion of the secondary bone plate and the rest of the plate. In certain embodiments, the angle between the engagement element of the secondary bone plate and the rest of the plate may range from about 1° to about 90°, such as from about 5° to about 45°, for instance from about 7.5° to about 30°, including from about 10° to about 20°, such about as 15°. However, in certain embodiments, the engagement element positioned at the proximal portion of the secondary bone plate is not angled but rather is planar with respect to the distal end of the secondary bone plate.

In certain embodiments, the proximal portion and/or engagement element of the secondary bone plate includes one or more openings, such as an opening that spans the thickness of the secondary bone plate and extends between a bone contacting surface and a top surface thereof. For instance, in certain embodiments, the engagement element of the secondary bone plate is configured as, or includes, an opening positioned in the proximal portion of the plate that is adapted for receiving a fastener, such as a fastener that may be inserted through the opening and functions to couple the secondary bone plate to one or more of a additional, e.g., primary, plate or a bone portion, e.g., a second bone portion.

This opening, as described above, may be of any suitable configuration, for instance, the opening may be round, e.g., circular or semi-circular, triangular, square, ovoid, elliptical, or the like. For example, in certain embodiments, the opening is circular and in certain embodiments the opening is semi-circular, arced, or ovoid, as described above with reference to the primary bone plate. In certain embodiments, two or more openings are included and positioned at the proximal portion of the primary bone plate.

Accordingly, in certain embodiments, the proximal portion of the secondary bone plate is configured for being attached to a bone portion, e.g., a secondary bone portion. Hence, in certain embodiments, the secondary bone plate includes one or more openings, which openings are adapted so as to receive a fastener so as to attach the bone plate to a bone portion, wherein the configurations and dimensions of the openings are equivalent to those described above, and wherein the openings are positioned in an intercalating and/or distal portion of the secondary bone plate.

The distal body portion of the secondary bone plate may include an opening that is configured for receiving a fastener, such as a fastener that is adapted so as to attach the secondary bone plate to a bone portion, e.g., a third bone portion. In certain embodiments, one or more openings, as described herein, include threading such as threading that corresponds to threading positioned on a fastener. In this manner, a fastener may be inserted into and through the opening by rotating the fastener in such a manner that the threads of the fastener align with the corresponding threads of the opening. In certain embodiments, one or more openings do not include threading such that the fastener may be inserted there through without threading the fastener into the opening. In certain embodiments, the secondary bone plate includes an intercalating portion.

The secondary bone plate may be configured for being associated with, e.g., contacted with and/or attached to a bone portion, such as an articulated portion of a bone, for instance, as a metaphyseal or epiphyseal bone portion. For example, in certain embodiments, the secondary bone plate may be configured for being attached to a periarticular or juxta-articular portion of a bone, and therefore, the secondary bone plate may be referenced as a periarticular or juxtaarticlar bone plate. Hence, in certain embodiments, the secondary bone plate, e.g., a periarticular bone plate, may be configured so as to be complimentary to a bone morphology, such as the articulated bone morphology of a metaphysis or epiphysis bone portion. Accordingly, in certain embodiments, the periarticular bone plate has a configuration that is complimentary to a non-planar portion of an articulated bone portion.

For instance, in certain embodiments, the secondary bone plate may have a configuration that is adapted to conform to a specific bone morphology, such as a configuration that is adapted to specifically and snugly fit the bone morphology to which the secondary bone plate is to be contacted, associated, and/or attached. Thus, in certain embodiments, the secondary bone plate is non-planar. Consequently, in certain embodiments, there is an angle between the proximal and distal portions of the secondary bone plate.

For example, in certain embodiments, a bone contacting surface of a proximal portion of a secondary bone plate may constitute a first or proximal plane of the secondary bone plate, and a bone contacting surface of a distal portion of a secondary bone plate may constitute a second or distal plane of the secondary bone plate, wherein the proximal and distal planes of the secondary bone plate are transverse to one another. Hence, in certain embodiments, the bone contacting surface between the proximal and distal portions and/or ends thereof of the secondary bone plate may include an internal angled portion. Accordingly, in certain embodiments, the angle between the planes defined by the proximal and distal bone contacting surfaces of the secondary bone plate may range from about 1° to about 90°, such as from about 5° to about 45°, for instance from about 7.5° to about 30°, including from about 10° to about 20°, such about as 15°. Additionally, although there may be an angle between the proximal and distal portions of the secondary bone plate, in certain embodiments, the proximal portion of the secondary bone plate is not angled with respect to a primary plane as defined by the primary bone plate. For instance, in certain embodiments, the proximal portion of the secondary bone plate is substantially coplanar with a primary plane of the primary bone plate, such that the two bone plates are capable of interfacing with one another in plane, e.g., that is within the same plane.

In certain embodiments, the secondary bone plate includes an internal angled, curved, and/or arced portion between the proximal and distal ends thereof and is therefore angled, curved and/or arced in correspondence to a bone surface to which the plate is to be associated so as to model the morphology of the bone surface. Hence, in certain exemplary embodiments, the bone contacting surface between the proximal and distal ends of the secondary bone plate may include an internal curved portion, wherein the curve includes a degree of curvature that ranges from about 10 mm to about 50 mm, for instance, between about 15 mm to about 35 mm, such as between about 18 mm or about 20 mm to about 25 or about 30 mm.

The bone contacting surface between the proximal and distal ends of the secondary bone plate may include an internal arced portion, wherein the arc includes a radius of curvature that may be constant, increasing, or decreasing, depending in part on the length of the intercalating portion of the secondary bone plate. Accordingly, in certain embodiments, a bone contacting surface of the secondary bone plate includes an arc that has a decreasing radius of curvature that ranges from about 10 mm to about 50 mm, for instance, between about 15 mm to about 35 mm, such as between about 18 mm or about 20 mm to about 25 or about 30 mm. In certain embodiments, the secondary bone plate includes a curved and/or twisted portion whereby the twisted portion allows the secondary bone plate to extend outward and away from a primary bone plate so as to contact a bone surface that is positioned distally and out of plane with a bone contacting surface and/or a primary plane of the primary bone plate.

In certain embodiments, the secondary bone plate includes a curved or concave portion between the first and second sides thereof and is therefore curved relative to a central, longitudinal axis defined by the proximal and distal ends of the secondary bone plate. For instance, in certain embodiments, the secondary bone plate may include an internal concave portion between the first and second sides of the bone plate. The concaved portion may run along a partial or entire length of the secondary bone plate, wherein the curvature comprises a degree of curvature, e.g., a concavity, that ranges from about 5 mm to about 30 mm, for instance, between about 8 mm to about 30 mm, such as between about 10 mm or about 12 mm to about 20 mm or about 25 mm. In certain embodiments, the proximal portion includes a concaved portion, while the distal portion does not, e.g., a portion between the first and second sides of the secondary bone plate along the distal portion of the secondary bone plate are substantially flat or planar, and in certain embodiments, the distal portion includes a concaved portion, while the proximal portion does not.

In certain embodiments, the secondary bone plate of the bone plate system includes a distal portion that is angled, curved, or arced, as described above, relative to a proximal portion, wherein the proximal portion of the secondary bone plate is relatively planar in relation to a primary plane defined by a top or bone contacting surface of the primary bone plate.

In other embodiments, the proximal portion is angled, curved, or arced with respect to a primary plane defined by a top or bone contacting surface of the primary bone plate, but is in plane internally with respect to the distal portion of the secondary bone plate, that is the distal and proximal ends of the secondary bone plate may be in plane with one another (e.g., thus forming a secondary plane there between), which plane may transect or otherwise be out of plane from the primary plane of the primary bone plate. Accordingly, a portion or the entire secondary bone plate may be angled or curved with relationship to the primary bone plate.

In view of the above, the secondary bone plate may be angled in relationship to the primary bone plate in numerous ways such that the secondary bone plate, e.g., a periarticular or juxtaarticular bone plate, includes a bone contacting surface that corresponds to one or more planes or an arc that are provided at an angle or substantially perpendicular to a primary plane defined by a primary bone plate. Accordingly, in certain embodiments, the secondary bone plate is angled with respect to a primary plane defined by the primary bone plate, wherein the angle may range from about 1° to about 90°, such as from about 5° to about 45°, for instance from about 7.5° to about 30°, including from about 10° to about 20°, such about as 15°.

In certain embodiments, the secondary bone plate includes a plurality of sections. For instance, in certain embodiments, the secondary bone plate may include a first section, wherein the first section includes a primary bone plate engagement element, and a second section, wherein the second section includes a configuration adapted for contacting a bone surface. In certain embodiments, the second section is transverse to the second section.

For example, in certain embodiments, the secondary bone plate may be configured so as to have a substantially "T" shape. Specifically, the first section may include a proximal portion with a proximal end, a distal portion with a distal end, and an intercalating portion; and the second section may be transverse to the first section and may include a proximal portion with a proximal end, a distal portion with a distal end, and an intercalating portion, wherein the intercalating portion, or another portion, of the second or transverse section is bisected by the distal portion of the first section, such that the secondary bone plate forms a "T" shape.

In certain embodiments, the first section of the secondary bone plate is angled in relation to the second section. For instance, a top or bottom surface of the proximal portion of the first section may define a first plane, and a top or bottom surface of the distal portion of the first section and/or a top or bottom surface of the second section may define a second plane, wherein the first and second planes transect one another, such that the second section is out of plane of the first section.

Accordingly, in certain embodiments, a portion or the entire first section of the secondary bone plate may be angled with respect to a portion or the entire second section of the secondary bone plate, wherein the angle may range from about 1° to about 90°, such as from about 5° to about 45°, for instance, from about 7.5° to about 30°, including from about 10° to about 20°, such about as 15°. In this manner, the secondary bone plate may have a "T" shaped configuration and may be configured so as to be associated with the primary bone plate, and further may be configured so as to contact a bone surface wherein the bone surface has an angled or curved morphology with respect to the plane of the primary bone plate.

The proximal and/or distal portions of the second section of the secondary bone plate may be curved or angled with respect to the intercalating portion and/or each other. For instance, in certain embodiments, the second section may include a curvature, which curvature may span a portion or the entire length of the second section. In certain embodiments, one or more of the portions of the second section of the secondary bone plate are angled with respect to each other, wherein the angle may range from about 1° to about 90°, such as from about 5° to about 45°, for instance, from about 7.5° to about 30°, including from about 10° to about 20°, such about as 15°.

As summarized above, in certain aspects, the subject bone plate system includes a bone fixation element, such as a fastener of the disclosure. A bone fixation element of the subject disclosure may include an extended body. In certain variations, the extended body includes a proximal portion including a proximal end, a distal portion including a distal end, and an elongate portion extending between said proximal and distal portions.

In certain variations, the proximal portion includes a shaft, wherein the shaft includes at least one smooth region and at least one threaded region. In certain variations, the smooth region may be positioned between the proximal end and the threaded region and may include a length that corresponds to a thickness of a bone plate, e.g., a primary or extender bone plate.

In certain variations, the threaded region includes locking screw threads and may include a length that corresponds to a thickness of a bone plate, e.g., a primary or extender bone plate.

In certain variations, the proximal end may be configured for engaging a top surface of a bone plate. The elongate portion may or may not include threading and the distal portion may be conical in shape and tapered such that the distal end forms a point. Further, the fastener may include small projections or teeth that are configured for engaging the bone plate and/or extender, for instance, on each side. In certain embodiments, the fastener may include a smooth surface, and in certain embodiments, the surface may be knurled.

Accordingly, a bone plate of the disclosure may include an opening that may be aligned with a corresponding opening in another bone plate and be adapted to receive a fastener, such as a bone fixation element disclosed herein, which fastener may be inserted through the opening in one bone plate and into a corresponding opening in another bone plate, thereby associating the bone plates together, and in some instances, securing the two bone plates to a bone portion, thereby not only securing the bone plates together, but also securing both bone plates to the bone.

As summarized above, the bone plate system of the present disclosure may be employed to reduce and/or fix one or more bone portions for the treatment of a bone fracture, for example. Reference will now be made in detail to various embodiments of the disclosure, which are illustrated in the accompanying figures. Referring now to FIGS. 1-7, a bone plate system of the present disclosure may include a plurality of bone plates. For instance, the bone plate system may include a primary bone plate such as a bone plate positioned at a diaphyseal bone portion proximal to the locus of the bone fracture, which bone plate may be termed a diaphyseal or proximal bone plate. Additionally, the bone plate system may include a secondary bone plate such as a bone plate positioned at a periarticular bone portion distal to the locus of a bone fracture, which bone plate may be termed a periarticular or distal bone plate. The bone plates of the bone plate system may be configured for being attached to one or more bone portions and may be adapted to be coupled together with one another so as to reduce, fix and/or stabilize one or more bone portions in correct anatomical and/or healing alignment for the treatment of a bone fracture.

As shown in FIGS. 1A-1E, the bone plate system 10, includes a first, or primary bone plate 20, and a second, or secondary bone plate 30. As depicted, the primary bone plate 20 is elongated, substantially planar, and includes a distal portion 22 with a distal end 23, a proximal portion 25 with a proximal end 26, and an intercalating portion 24 between the distal and proximal portions.

Additionally, the primary bone plate includes a first side 27 and a second side 28 as well as bone contacting surface 21 and a top surface 29. The distal portion 22 is configured for engaging at least a portion of a secondary bone plate 30 and/or a portion of bone, and therefore, includes a secondary bone plate engagement element 19a. The secondary bone plate engagement element 19a is configured as a hooded, slotted tab receiving portion.

The primary bone plate 20 additionally includes a plurality of openings 15a-e. Openings 15a and 15b are circular and positioned in the proximal portion 25 of the primary bone plate 20. Opening 15c is oval and aligned in the longitudinal direction of the intercalating portion 24 of the primary bone plate 20. Openings 15d and 15e are positioned in the distal portion 22 of the primary bone plate 20. Opening 15d is circular and opening 15e is oval and aligned in the transverse direction, relative to axis 1. The openings 15a-15e extend between the bone contacting surface 21 and the top surface 29, may be recessed, and are configured for receiving a fastener there through. It is to be understood that more or less openings than illustrated may be provided. Additionally, as can be seen with reference to FIG. 1, the top surface 29 of the primary bone plate substantially corresponds to a primary plane 1.

The secondary bone plate 30 is elongated, non-planar, and includes a proximal portion 32 with a proximal end 33, a distal portion 35 with a distal end 36, and an intercalating portion 34 between the distal and proximal portions. Additionally, the secondary bone plate includes a first side 37 and a second side 38 as well as bone contacting surface 31 and a top surface 39. The proximal portion 32 is configured for engaging at least a portion of a primary bone plate 30 and a portion of bone, and therefore is configured as a primary bone plate engagement element 19b, which is configured as a tab insertion portion.

The secondary bone plate 30 additionally includes a plurality of openings such as 15f, 15g, and 15h. Openings 15f and 15g are positioned in the proximal portion 32, and openings collectively numbered as 15h are positioned in the distal portion 35 of the bone plate 30. The openings are circular, extend between the bone contacting surface 31 and the top surface 39, and are configured for receiving a fastener there through. Again, it is to be noted, that more or less openings than illustrated may be provided.

As can be seen with reference to FIG. 1A, the distal portion 22 of the primary bone plate 20 is configured for being coupled to the proximal portion 32 of the secondary bone plate 30. Accordingly, the proximal portion 22 of the primary bone plate 20 includes a secondary bone plate engagement element 19a, which engagement element is configured as a recessed and hooded slot portion within the primary bone plate 20. As depicted, the recessed portion is tapered and configured so as to form a slot. Further, the proximal portion 32 of the secondary bone plate 30 includes a primary bone plate engagement element 19b, which engagement element is configured as an extended or tab portion positioned at the proximal end 33 of the secondary bone plate 30, which tab portion is configured for being received within the slot portion of primary bone plate 20.

The primary bone plate engagement element or tab portion 19b of the secondary bone plate is adapted to fit within the secondary bone plate engagement element or slot portion 19a of the primary bone plate so as to allow the secondary bone plate 30 to be coupled to the primary bone plate 20. In such a configuration, openings 15d and 15e on the primary bone plate 20 may be aligned with openings 15f and 15g on the secondary bone plate 30, and suitable fasteners inserted there through so as to attach the primary and secondary bone plates together and/or to a surface of a bone.

Figure 1B:
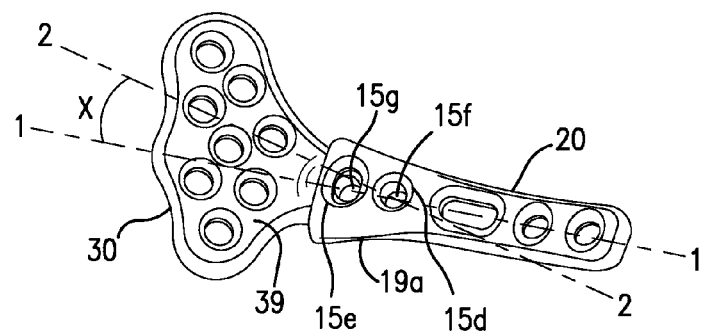
FIG. 1B provides a perspective view of a top surface of the bone plate system of FIG. 1A, wherein the bone plate system includes a primary bone plate and a secondary bone plate coupled together.

As can be seen with reference to FIG. 1B, a primary bone plate 20 and a secondary bone plate 30 are provided wherein the primary 20 and secondary 30 bone plates are coupled together. As depicted, the primary bone plate 20 includes a secondary bone plate engagement element 19a that is configured as a hooded slot. The secondary bone plate 30 includes a primary bone plate engagement element 19b that is configured as an extended tab portion that is configured for being received within the hooded slot portion of primary bone plate 20. Accordingly, the primary 20 and secondary 30 bone plates may be coupled together by insertion of the tab portion 19b into the hooded slot portion 19a so that openings 15g and 15f align with openings 15e and 15d. The two bone plates may then be attached to one another and to an underlying bone portion by insertion of fasteners through the aligned openings.

Figure 1C:
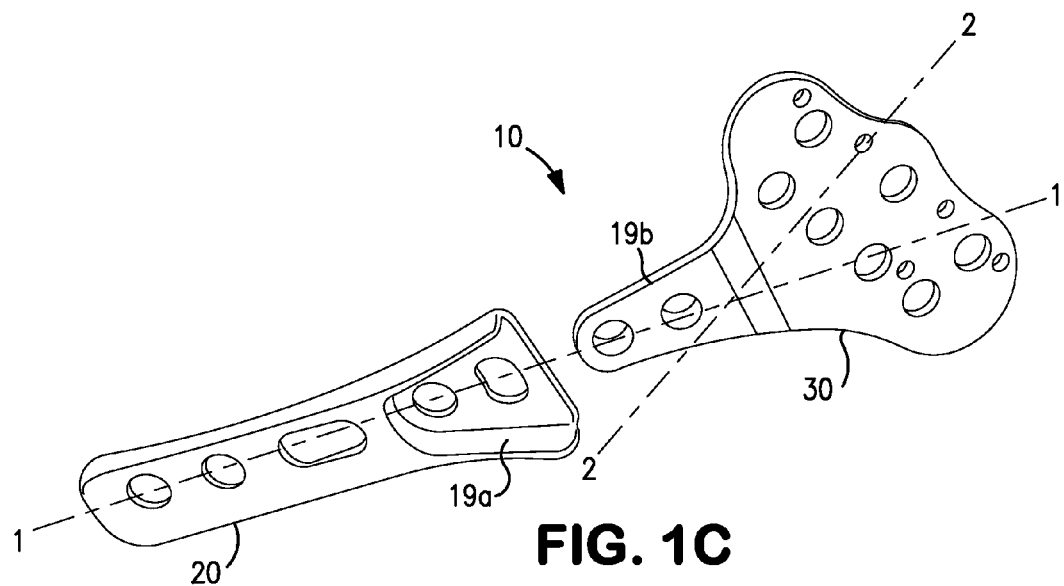
FIG. 1C provides a bottom view of the bone plates of FIG. 1A.
Figure 1D:
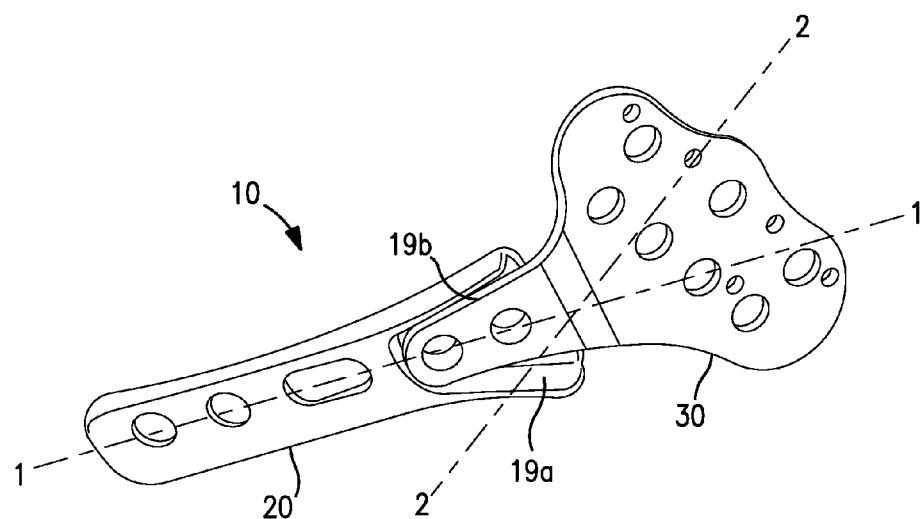
FIG. 1D provides a bottom view of the bone plates of FIG. 1B.
Figure 1E:
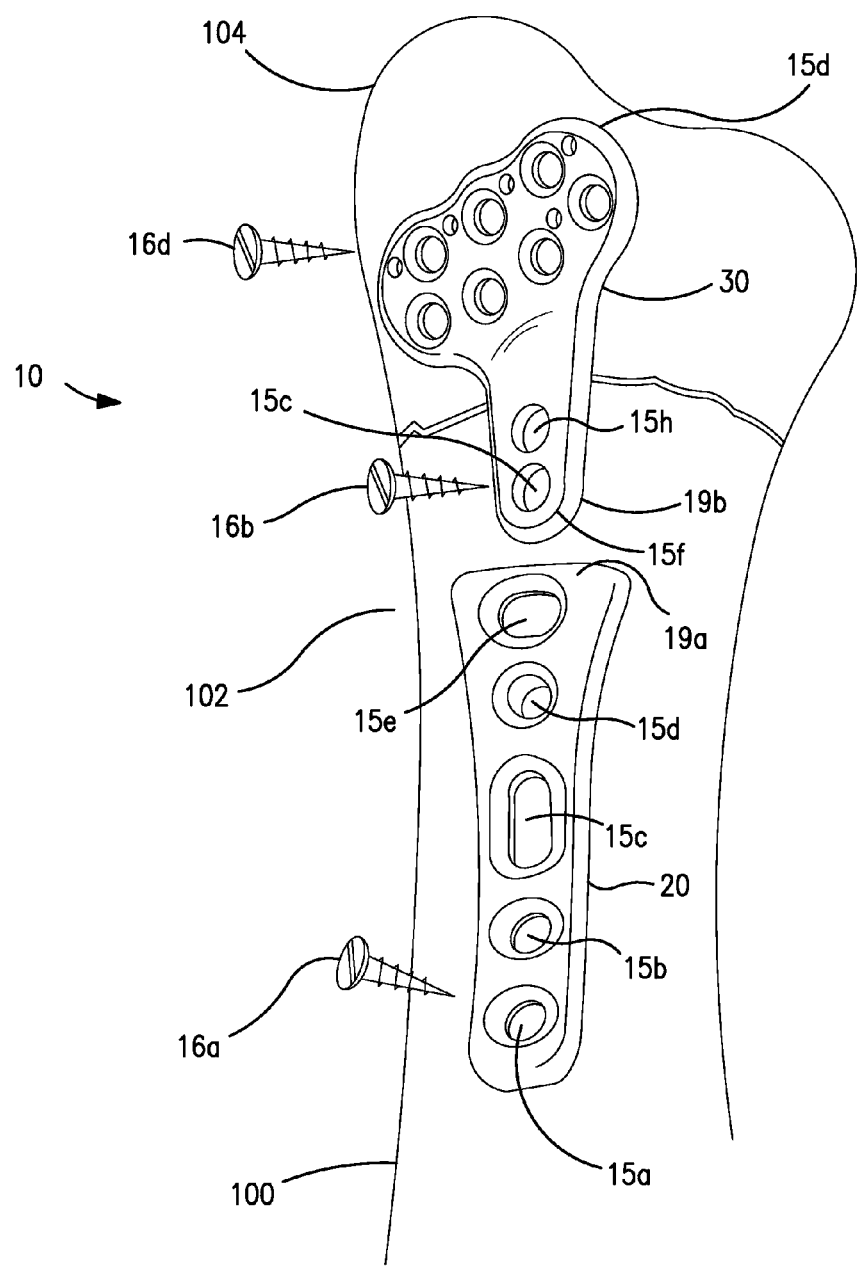
FIG. 1E provides the bone plate system of FIG. 1A, wherein the primary and secondary bone plates are attached to respective bone portions, prior to coupling of the bone plates.
Figure 1F:
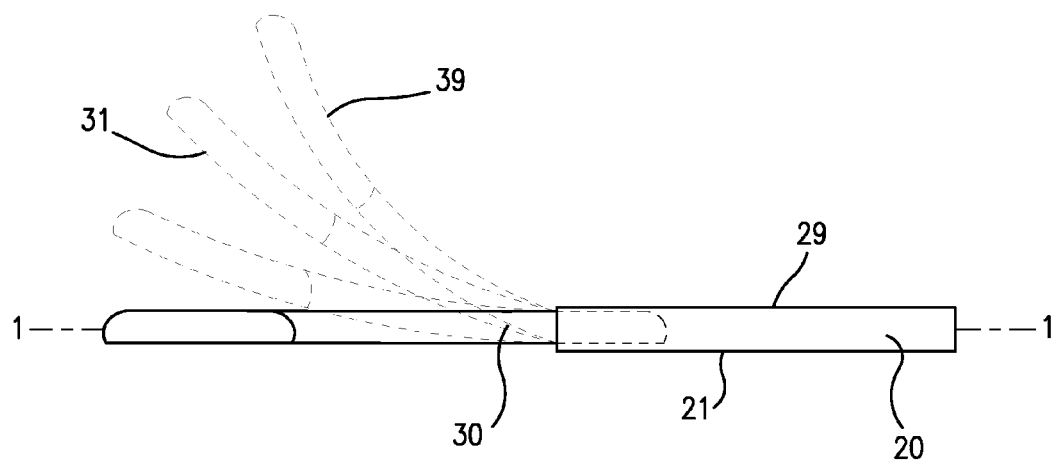
FIG. 1F provides a side view of a bone plate system as described herein, wherein the secondary bone plate is curved or bent.
Figure 1G:
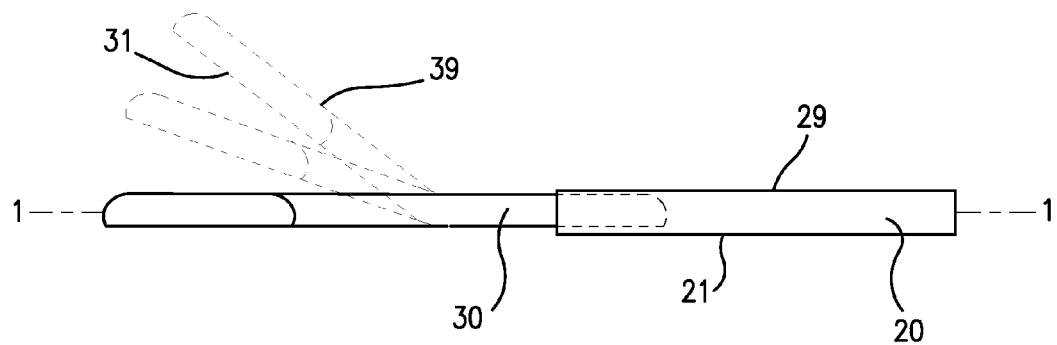
FIG. 1G provides a side view of a bone plate system as described herein, wherein the secondary bone plate is angled with respect to a top surface of the primary bone plate.
Figure 1H:
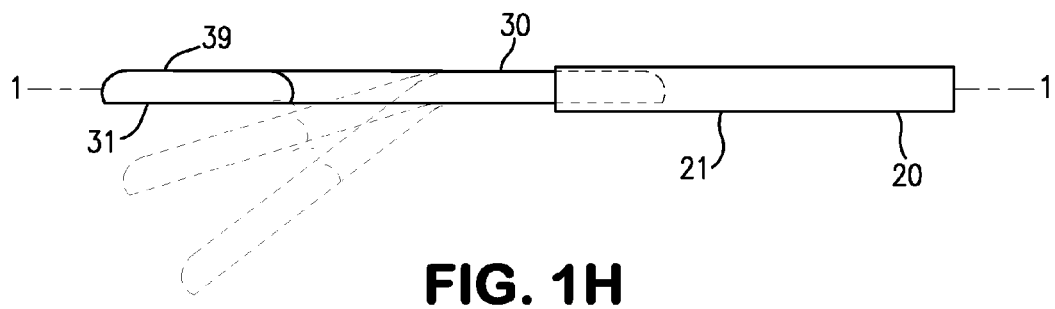
FIG. 1H provides a side view of a bone plate system as described herein, wherein the secondary bone plate is angled with respect to a bottom surface of the primary bone plate.

FIGS. 1C and 1D represent bottom views of the bone plates of FIGS. 1A and 1B, respectively. Specifically, FIG. 1C illustrates a bottom view of the primary bone plate 20 and secondary bone plate 30 of FIG. 1A, prior to the bone plate engagement elements 19a and 19b being coupled together. As can be seen with reference to FIG. 1C, the primary bone plate 20, is slightly concaved. FIG. 1D illustrates a bottom view of the primary bone plate 20 and secondary bone plate 30 of FIG. 1B, after the engagement elements 19a and 19b of the two bone plates have been coupled together. Additionally, as depicted, a top surface of primary bone plate 20 corresponds to a primary plane 1, and a top surface of the secondary bone plate 30 corresponds to a secondary plane 2, wherein the primary plane 1 and the secondary plane 2 are transverse and transect one another, for instance, at an intercalating portion of the secondary plate, so as to form an angle there between.

Accordingly, the bone plate system 10 may be applied to one or more bone portions so as to align, reduce, and/or stabilize a bone fracture. For instance, as can be seen with reference to FIG. 1E, a secondary bone plate 30 may be positioned along a second bone portion 104, such as a juxta-articular or metaphyseal bone portion of the radial side of radius bone 100, distal to the locus of a fracture. As illustrated, the configuration of the secondary bone plate 30 is adapted so as to model the morphology of the bone region of the distal radius to which the secondary bone plate is attached and therefore includes an internal arced or curved portion, denoted by the two curved lines on bone plate 30. One or more fasteners, such as 16d, may be inserted into one or more of the openings, such as 15d, in the secondary bone plate 30, so as to attach the bone plate 30 to the second portion of bone 104. The secondary bone plate 30 may then be used to align and reduce the second bone portion 104 with respect to a first bone portion 102.

Likewise, a primary bone plate 20 may be positioned along the first bone portion 102, such as a long or diaphyseal bone portion, of a bone 100. For instance, as depicted, the primary bone plate 20 may be positioned on the radial side of a diaphyseal portion of the radius bone of the left arm proximal to the locus of a fracture. The primary bone plate may also be positioned on a dorsal or volar surface, dependent on the configuration of the bone plate and the locus of the fracture.

Once the primary and secondary bone plates 20 and 30 have been appropriately positioned with respect to bone portions 102 and 104, the bone plate engagement elements 19a and 19b of the primary and secondary bone plates, respectively, may be aligned and coupled to, e.g., inserted into, one another so as to reduce the two bone portions 102 and 104. Fasteners, such as 16a, may be inserted into one or more of openings 15a-c of the primary bone plate so as to attach the bone plate 20 to the first portion of bone 102, and fasteners, such as 16b, may then be inserted through aligned openings 15d-15h to attach the two bone plates together and thereby stabilize the fractured bone portions.

Additionally, as can be seen with reference to FIG. 1, the top surface 39 of the secondary bone plate substantially corresponds to a secondary plane 2, which secondary plane 2 transects the primary plane 1 at an angle x. Specifically, as can be seen with reference to FIGS. 1F to 1H, the top surface 39 or bone contacting surface 31 of the secondary bone plate 30 may correspond to one or more planes or an arc, which are provided as a curvature or an angle to the primary plane 1 of a top surface 29 or bone contacting surface 21 of the primary bone plate 20. The secondary bone plate may be arced, curved, and/or angled, as described above, in a variety of manners with respect to the primary plane 1.

FIG. 2 illustrates the use of the bone plate system of FIG. 1. As illustrated in FIG. 2, a distal portion 104 of radius bone 100 is fractured and displaced with respect to a diaphyseal portion 102 of the radius bone 100. As can be seen with respect to FIG. 2A, the bone plate system 10, includes a secondary bone plate 30. The secondary bone plate 30 is non-planar and includes a top surface 39, a bone contacting surface 31, and additionally includes a primary bone plate engagement element 19b configured as a bent tab member. As depicted, the secondary bone plate 30 is positioned along a second bone portion 104 shown here as the dorsal surface of a juxta-articular/metaphyseal bone portion, distal to the fracture site, of a radius bone 100. The distal portion 35 of the secondary bone plate 30 includes openings that are configured for receiving fasteners 16h-n there through, which fasteners pass through the opening and are inserted into the bone 104.

Figure 2B:
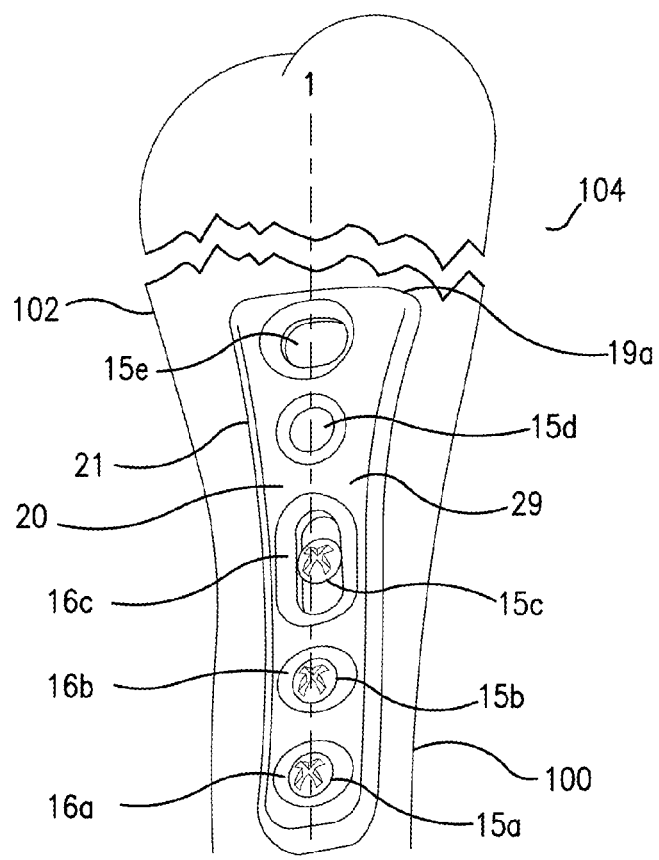
FIG. 2B provides a perspective view of a primary bone plate attached to a bone portion.
Figure 2A:
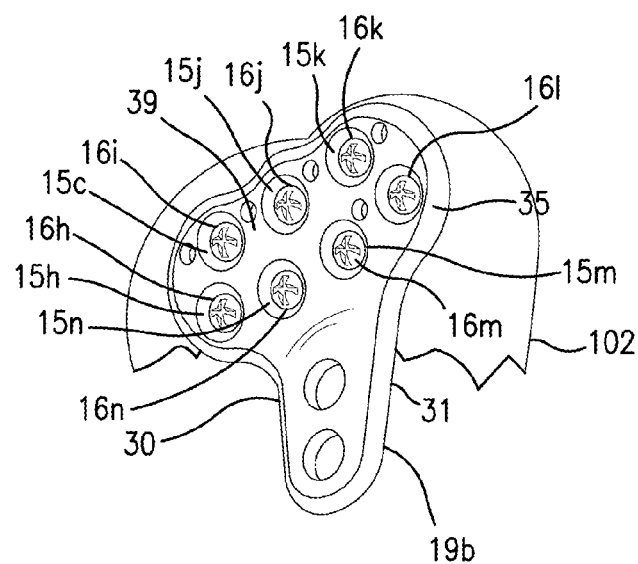
FIG. 2A provides a perspective view of a secondary bone plate attached to a bone portion, wherein the secondary bone plate includes an angled tab insertion portion.

As can be seen with reference to FIG. 2B, the bone plate system also includes a primary bone plate 20. The primary bone plate 20 includes a substantially planar top surface 29 with a primary bone plate engagement element 19a, configured as a hooded slot tab receiving element. Additionally, primary bone plate 20 includes a bone contacting surface 21, which surface defines a primary plane 1. The primary bone plate 20 includes openings, such as 15a-15e, and may be attached to a bone portion 102, such as a diaphyseal bone portion, via the insertion of fasteners, such as 16a-16c, through openings 15a-c. As depicted, the primary bone plate 20 is positioned along a first bone portion 102 shown here as the dorsal surface of the diaphyseal bone portion, proximal to the fracture site, of a radius bone 100. Fasteners 16a-16c are inserted into openings 15a-15c thereby attaching the bone plate 20 to the first portion of bone 102.

Figure 2C:
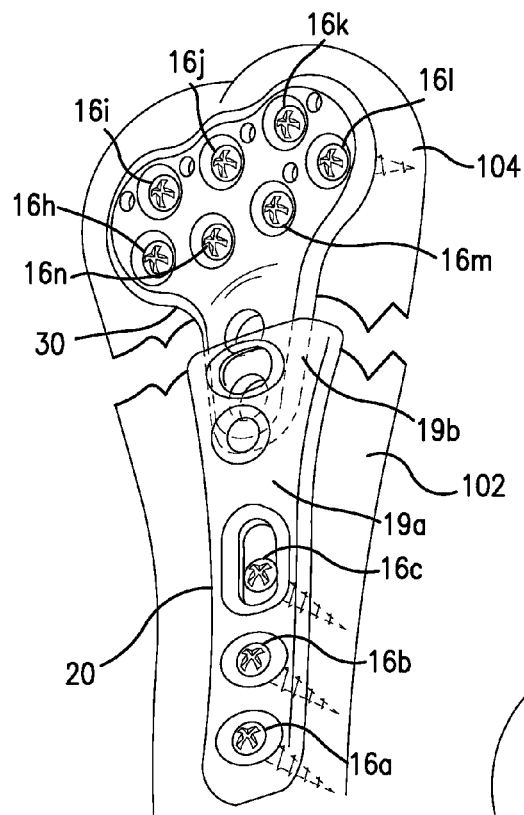
FIG. 2C provides a perspective view of the bone plate system of FIGS. 2A and 2B, wherein the primary and secondary bone plates are attached to respective bone portions and in the process of being coupled together but are not attached to one another.
Figure 2D:
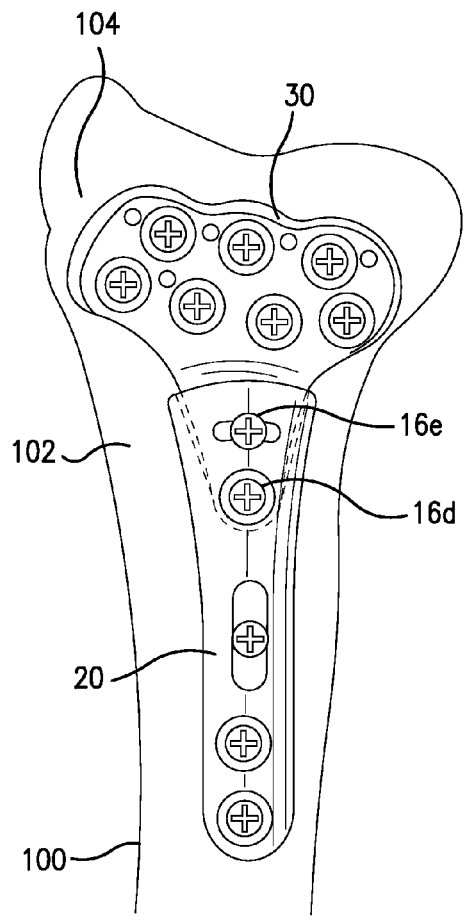
FIG. 2D provides a perspective view of the bone plate system of FIG. 2C, wherein the primary and secondary bone plates are attached to respective bone portions, coupled together, and attached to one another.

With reference to FIGS. 2C and 2D, the secondary bone plate 30 is positioned so as to contact and be attached to the fractured and displaced bone portion 104 of radius bone 100. The primary bone plate 20 is positioned and attached to bone portion 102 of radius bone 100 via fasteners 16a-16c. When properly aligned, fasteners 16h-m may be inserted through openings 15h-15n so as to attach the secondary bone plate 30 to the fractured distal radius bone portion 104. The two plates may then be coupled together by aligning the angled tab member 19b of bone plate 30 with the tab receiving member 19a (shown as cut-out portion) of bone plate 20, so as to reduce the two bone portions 104 and 102 into an alignment that at least approximates the natural anatomical morphology of bone 100. Once properly aligned and reduced, fasteners 16d and 16e may be inserted through the openings in the plates so as to join plates 20 and 30 and thereby stabilize the bone fracture, as shown in FIG. 2D.

FIG. 3 illustrates a side view of the bone plate system of FIG. 1. As can be seen with respect to FIG. 3A, the bone plate system includes a primary bone plate 20 and a secondary bone plate 30. The primary bone plate 20 is substantially planar and includes a top surface 29, a bone contacting surface 21, and additionally includes a secondary bone plate engagement element 19a positioned at a distal portion 22 thereof. A primary plane 1 is defined by the bone contacting surface 21. The secondary bone plate 30 is non-planar and includes a top surface 39, a bone contacting surface 31, and additionally includes a primary bone plate engagement element 19b. The two bone plates are coupled to one another via the joining of the two engagement elements 19a and 19b one with the other.

The secondary bone plate 30 further includes a proximal portion 32, an intercalating portion 34, and a distal portion 35, wherein the distal portion 35 is angled with respect to the proximal portion 32. Additionally, as can be seen with reference to FIG. 3A, the bone contacting surface 31 of the distal portion 35 of the secondary bone plate 30 substantially corresponds to a secondary plane 2, which secondary plane 2 transects the primary plane 1 at an angle x.

As can be seen with reference to FIGS. 3B-3D, the bone plate system 10 of FIG. 3A is applied so as to align, reduce, and/or stabilize a bone fracture. For instance, as depicted in FIG. 3B, bone 100 includes a fracture, which fracture separates bone portion 102 from bone portion 104. As depicted in FIG. 3C, the secondary bone plate 30 is positioned along a second bone portion 104, such as a juxta-articular or metaphyseal bone portion of bone 100. The bone plate 30 can attach to a distal fragment of the distal radius 104 and be used to reduce and fix the distal bone portion to the more proximal portion 102 of the radius 100. As illustrated, the configuration of the secondary bone plate 30 is adapted so as to model the morphology of the bone region to which the secondary bone plate is attached. For instance, the secondary bone plate 30 is shaped to conform with the radial portion of the distal radius and is adapted to be attached to the fractured and displaced bone portion 104. Fastener 16h is inserted into opening 15h so as to attach the secondary bone plate 30 to the second portion of bone 104.

Likewise, the primary bone plate 20 is positioned along a first bone portion 102, such as a diaphyseal bone portion of radius long bone 100. The primary bone plate is positioned proximally and volarly on the distal radius and is configured so as to be coupled with and attached to the secondary bone plate 30, which bone plate is positioned distally and volarly on the distal radius. Fastener 16a is inserted into opening 15a thereby attaching the bone plate 20 to the first portion of bone 102.

The primary and secondary bone plates 20 and 30 may be appropriately positioned by aligning the bone plate engagement elements 19a and 19b of the primary and secondary bone plates together for coupling. Specifically, bone plates 20 and 30 are designed such that when appropriately attached to respective fractured bone portions, the fractured bone portions may be aligned into a healing alignment that approximates the bones natural anatomical morphology, simply by coupling the two bone plates with one another. Once coupled together, the two bone plates 20 and 30, may be attached to one another and/or the underlying bone portion via insertion of a fastener 16e through aligned openings 15e and 15g, so as to reduce the two bone portions 102 and 104 and thereby stabilize the fractured bone portions.

Figure 4C:
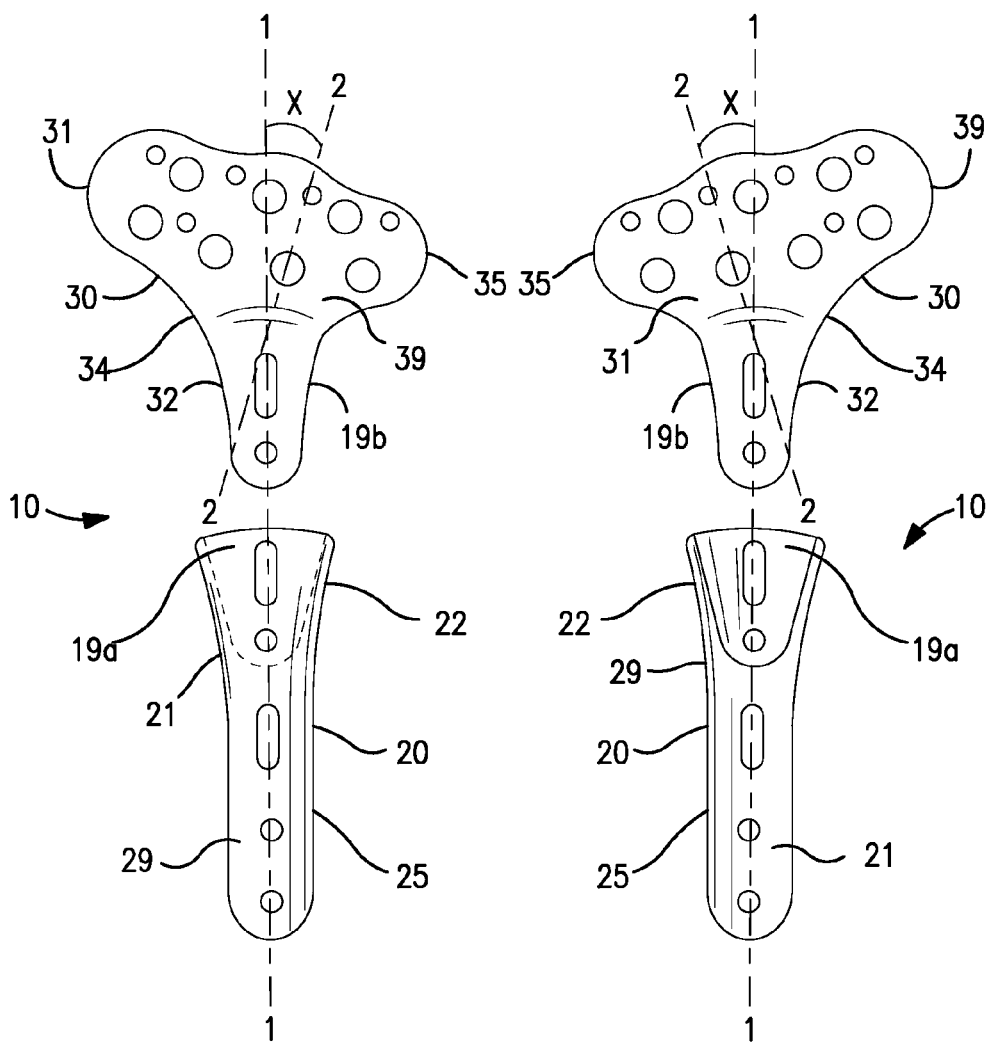
FIG. 4C provides a side view of a bone plate engagement element of a primary bone plate.
Figure 4C:
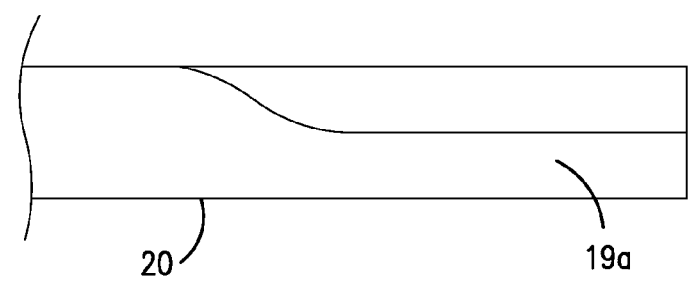

FIG. 4 illustrates another embodiment of the bone plate system of FIG. 1. FIG. 4A provides a top view and FIG. 4B provides a bottom view of the bone plate system 10. The bone plate system 10 includes a primary bone plate 20. The primary bone plate 20 includes a top surface 29 and a bone contacting surface 21, as well as a distal portion 22 and a proximal portion 25. The top surface 29 of the distal and proximal portions 22 and 25 is planar. Accordingly, the top surface 29 of the primary bone plate 20 is planar and defines a primary plane 1. The distal portion 22 additionally includes a secondary bone plate engagement element 19a, shown in detail in FIGS. 4B and 4C, wherein the engagement element 19a is configured as a hooded and recessed, "female" tab receiving portion that is configured for receiving a corresponding "male" tab insertion portion 19b of a secondary bone plate 30 so as to be coupled therewith. The tab receiving portion 19a is coextensive with the bottom surface 21.

The bone plate system of FIG. 4A further includes a secondary bone plate 30. The secondary bone plate 30 is non-planar and includes a proximal portion 32, an intercalating portion 34, and a distal portion 35. Bone plate 30 includes a top surface 39, a bone contacting surface 31, and further includes a primary bone plate engagement element 19b configured as a tapered "male" tab insertion member that is configured for being inserted within a corresponding "female" tab receiving portion 19a of a primary bone plate 20.

As can be seen with reference to FIG. 4, in certain embodiments, the proximal portion 32 and distal 35 portion of the secondary bone plate 30 may be angled with respect to the intercalating portion 34 and/or each other. For instance, the top surface 39 of the distal portion 35 of the secondary bone plate 30 may define a secondary plane 2, which plane transects the primary plane 1, at an angle x. Accordingly, in certain embodiments, the distal portion 35 of the secondary bone plate 30 is angled with respect to the proximal portion 32, wherein the angle x may range from about 1° to about 90°, such as from about 5° to about 45°, for instance, from about 7.5° to about 30°, including from about 10° to about 20°, such about as 15°. As depicted, the engagement element 19a is tapered in correspondence with the tapered engagement element 19b.

Further, as can be seen with reference to FIG. 4B, the secondary bone plate engagement element 19a of the primary bone plate 20, may include a hooded and recessed or slot portion such that when the engagement element 19b of the secondary bone plate 30 is inserted therein, the top surface 39 of the proximal portion 32 of the secondary bone plate 30 is aligned and/or flush with the top surface 29 of the primary bone plate 20.

As depicted, the distal portion 22 and proximal portion 32 of the primary and secondary bone plates, 20 and 30, respectively, include a plurality of openings, wherein one of the openings is circular and the other is ovoid. In at least this manner, the plate may be adjusted in the proximal/distal direction prior to locking the plate down. Hence, the ovoid opening allows the secondary bone plate 30 to be moved slightly, in a longitudinal direction, relative to the primary bone plate 20, before final fixation via the insertion of a fastener there through, whereby the two plates are locked together and additional longitudinal movement is prohibited.

FIG. 4C provides a side view of a bone plate engagement element 19a of a distal portion 22 of primary bone plate 20.

FIG. 5 illustrates another embodiment of the bone plate system of FIG. 1. FIG. 5A provides a top view and FIG. 5B provides a bottom view of the bone plate system 10. As can be seen with reference to FIG. 5A, the bone plate system 10 includes a primary bone plate 20 and a secondary bone plate 30. The primary bone plate 20 includes a top surface 29 and a bone contacting surface 21, as well as a proximal portion 25 and a distal portion 22 wherein the top surface 29 of the proximal and distal portions are planar with respect to one another. The distal portion 22 additionally includes a secondary bone plate engagement element 19a, wherein the engagement element 19a is configured as a recessed, "female" tab receiving portion that is configured for receiving a corresponding "male" tab insertion portion of a secondary bone plate so as to be coupled therewith. As depicted in FIG. 5B, the engagement element 19a is tapered in correspondence with the tapered engagement element 19b. Further, as depicted, the distal portion 22 of the primary bone plate 20 includes a plurality of openings, wherein one of the openings is circular 15d and the other opening is arced 15e.

The secondary bone plate 30 includes a top surface 39 and a bone contacting surface 31, as well as a proximal portion 32 and a distal portion 35, wherein the proximal and distal portions are angled with respect to one another. The proximal portion 32 additionally includes a primary bone plate engagement element 19b, wherein the engagement element 19b is configured as a tapered "male" tab insertion portion that is configured for being inserted within a corresponding "female" tab receiving portion of a primary bone plate. The proximal portion additionally includes two openings 15f and 15g, which are configured for receiving a fastener there through.

Figures 5A, 5B:
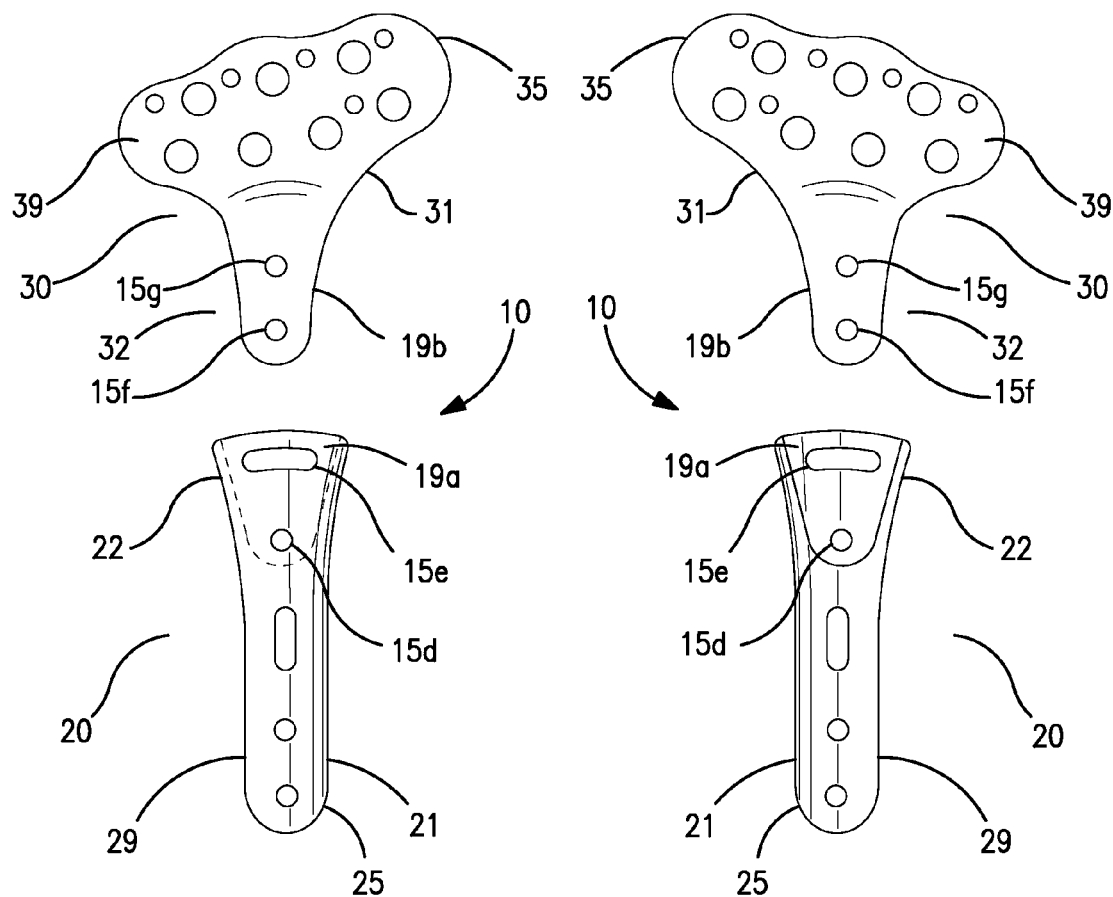
FIG. 5A provides a top view of a bone plate system as described herein, wherein the bone plate system includes a primary bone plate and a secondary bone plate prior to the coupling of the bone plates.
FIG. 5B provides a bottom view of the bone plate system of FIG. 5A.
Figure 5C:
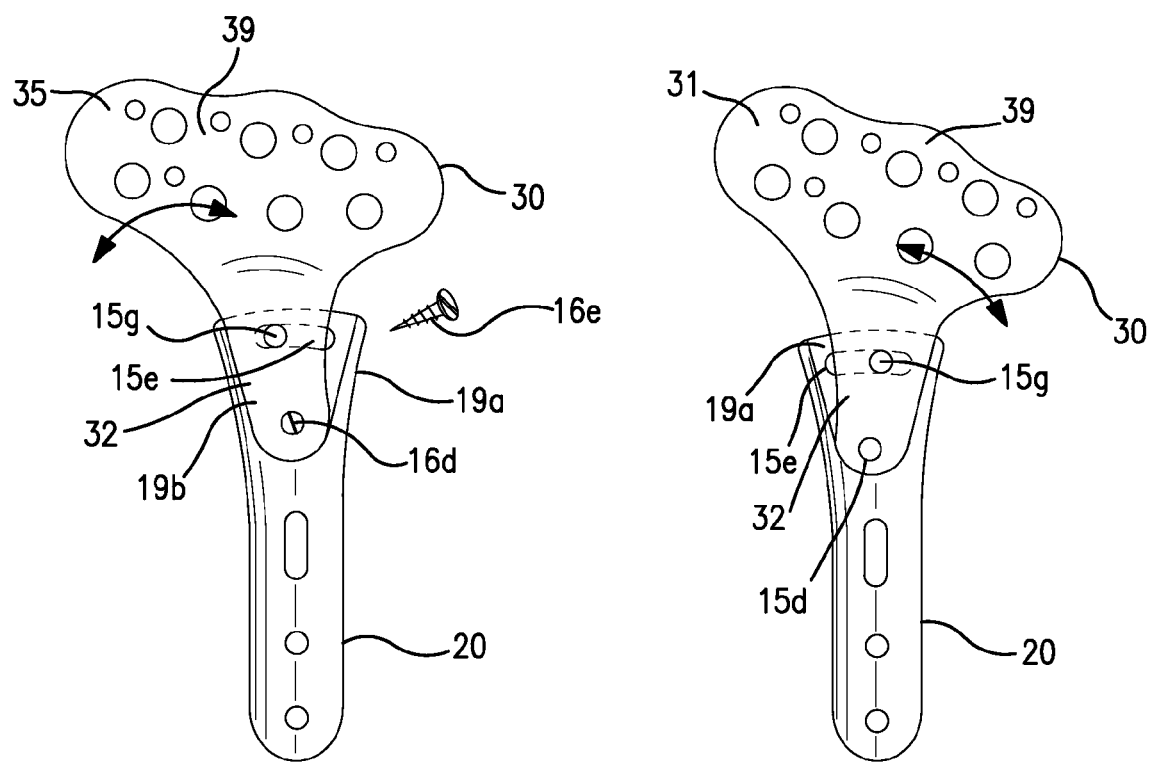
FIG. 5C provides a bottom view of the bone plate system of FIG. 5A, wherein the primary and secondary bone plates are coupled together, but the secondary bone plate may move slightly relative to the primary bone plate.

As illustrated in FIG. 5C, a fastener, 16d may be inserted into openings 15d and 15f, thereby affixing bone plates 20 and 30 to one another. However, due to the arced opening 15e, the secondary bone plate 30 is still capable of being moved or adjusted slightly, in a lateral direction, relative to the primary bone plate 20, before final fixation via the insertion of a fastener 16e through openings 15g and 15e, whereby the two plates are locked together and additional lateral movement is prohibited. Additionally, this configuration further allows the distal portion of the fracture to be reduced into its anatomical position.

Figure 5D:
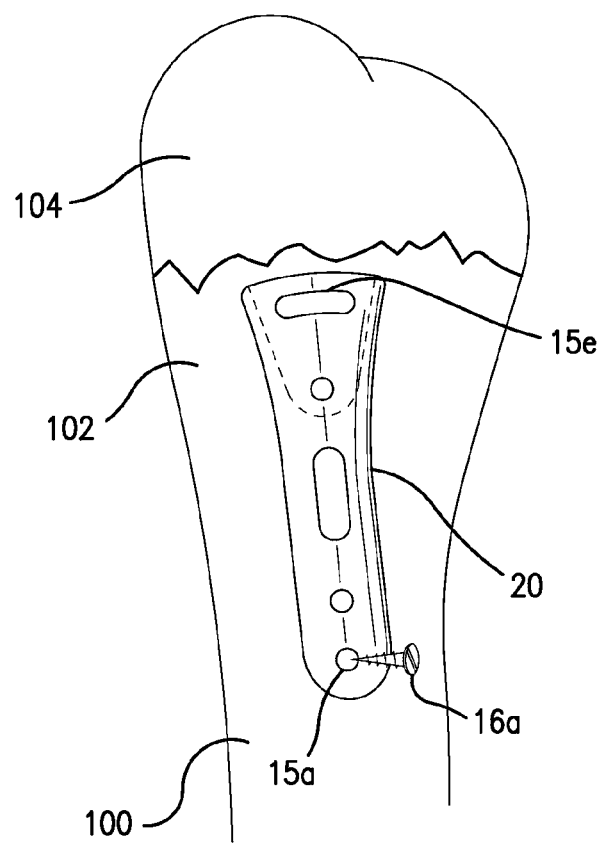
FIG. 5D provides a top view of the primary bone plate of FIG. 5A, wherein the primary bone plate is attached to its respective bone portion.
Figure 5E:
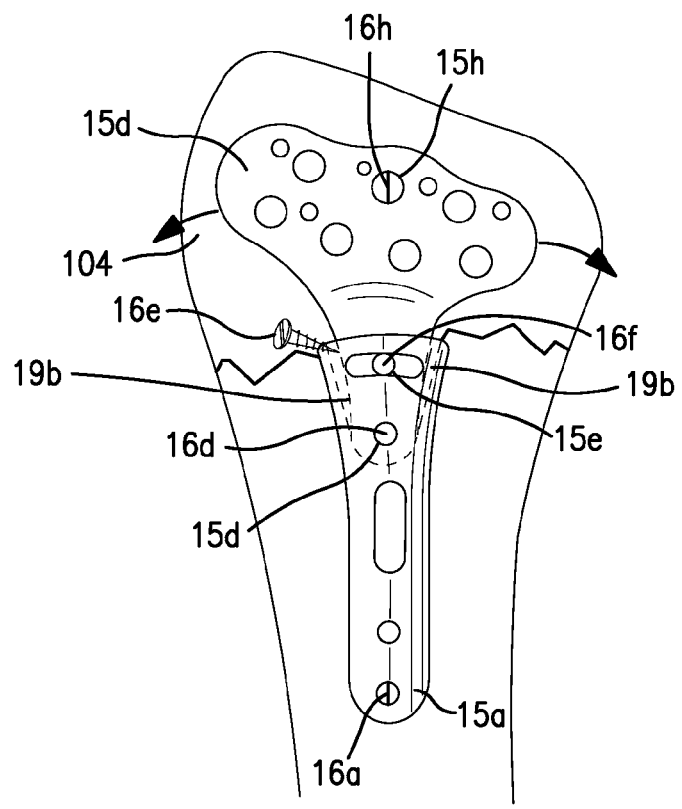
FIG. 5E provides a perspective view of the bone plate system of FIG. 5A, wherein the primary and secondary bone plates are attached to respective bone portions and coupled together.

As can be seen with reference to FIGS. 5D and 5E, a variation of the bone plate system 10 of FIG. 5A is applied so as to align, reduce, and/or stabilize a bone fracture. For instance, as illustrated in FIG. 5D, the primary bone plate 20 including arced opening 15e is positioned along a first bone portion 102, such as a long or diaphyseal bone portion of bone 100. For instance, as depicted, the primary bone plate is positioned on the volar surface of the distal radius, proximal to the fracture site. Fastener 16a is inserted into opening 15a thereby attaching the bone plate 20 to the first portion of bone 102.

Likewise, as illustrated in FIG. 5E, the secondary bone plate 30 is positioned along a second bone portion 104, such as a juxtararticular or metaphyseal bone portion of bone 100. For instance, as depicted the secondary bone plate is attached to the volar surface of the distal radius, distal to the fracture site. As illustrated, the configuration of the secondary bone plate is adapted so as to model the morphology of the bone regions to which the secondary bone plate is attached and, thus, is angled with respect to a bone contacting surface thereof. Fastener 16h inserted into opening 15h so as to attach the bone plate 30 to the second portion of bone 104.

The primary and secondary bone plates 20 and 30 are then appropriately positioned so that the bone plate engagement elements 19a and 19b of the primary and secondary bone plates are coupled together and attached to one another, e.g., via fastener 16d. In this configuration, and because of the arced shape of opening 15e, the secondary bone plate may move laterally relative to the primary bone plate 20 so as to properly reduce the two bone portions 102 and 104, whereby once the desired positioning has been achieved, fastener 16e may be inserted through openings 15e and 15g to lock the position of the plates and thereby stabilize the fractured bone portions. It is to be noted, that although with respect to FIG. 5D, the primary bone plate 20 is attached to the proximal bone portion 102 prior to attachment of the secondary bone plate 30 to the distal bone portion 204, in certain variations, this order of attachment is reversed.

Figure 6A:
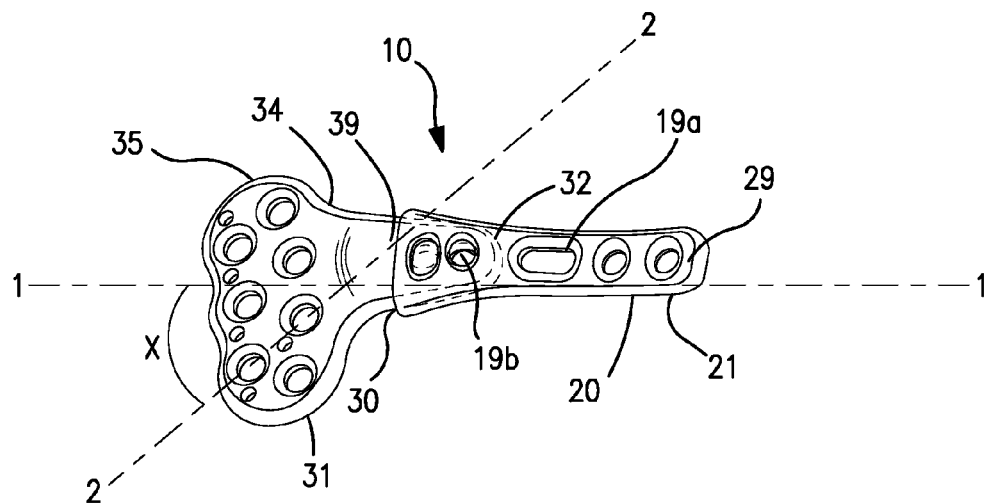
FIG. 6A provides a perspective view of a bone plate system as described herein, wherein the primary and secondary bone plates are attached to respective bone portions, subsequent to coupling of the bone plates.

FIG. 6 illustrates another embodiment of a bone plate system similar to that illustrated in FIG. 1. As can be seen with respect to FIG. 6A, the bone plate system includes a primary bone plate 20 and a secondary bone plate 30. The primary bone plate 20 includes a top surface 29 that is planar, a bone contacting surface 21, and additionally includes a secondary bone plate engagement element 19a, which is configured as a recessed and tapering slot that is configured for receiving a tab insertion engagement element 19b of a secondary bone plate 30. A primary plane 1 is defined by the bone contacting surface 21.

The secondary bone plate 30 is non-planar and includes a top surface 39, a bone contacting surface 31, and additionally includes a primary bone plate engagement element 19b, configured as an extended tab insertion element. The two plates are coupled to one another via the aligning and contacting of the two engagement elements one with the other and attached via the insertion of a fastener through openings therein.

The secondary bone plate 30 further includes a proximal portion 32, an intercalating portion 34, and a distal portion 35, wherein the distal portion 35 is angled with respect to the proximal portion 32, such that a plane, e.g., a secondary plane, defined by the bottom surface 31 of the distal portion 35 of the secondary bone plate 30, transects the primary plane 1 to form angle x. Thus, the distal portion of non-planar bone plate 20 is an angled with respect to the substantially planar bone plate 20.

Figure 6B:
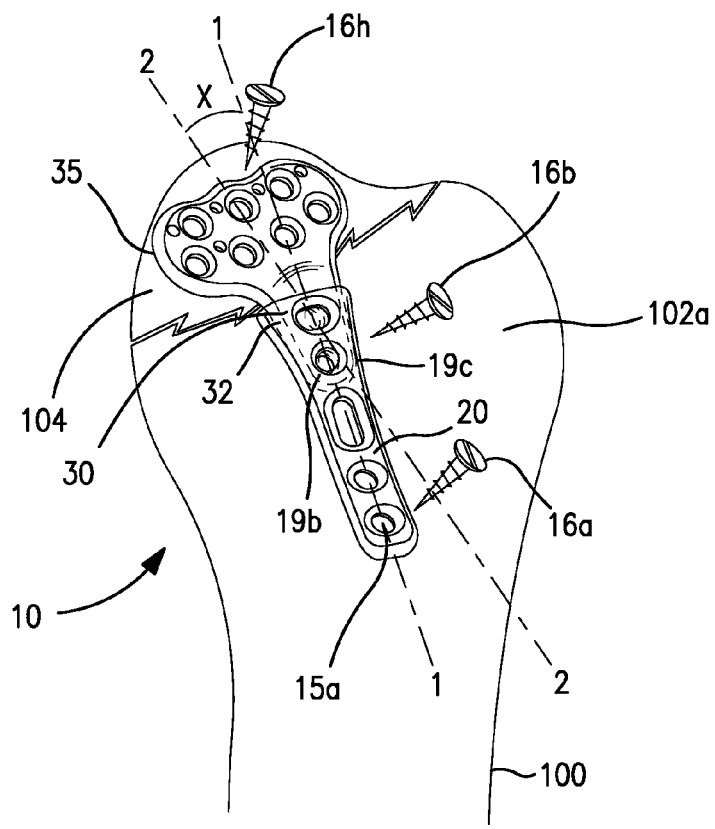
FIG. 6B provides a perspective view of the bone plate system of FIG. 6A, wherein the primary and secondary bone plates are attached to respective bone portions and coupled together.

As can be seen with reference to FIG. 6B, the bone plate system 10 of FIG. 6A is applied so as to align, reduce, and/or stabilize a bone fracture. For instance, the secondary bone plate 30 is positioned along a second bone portion 104, such as a juxtararticular or metaphyseal bone portion of bone 100. The distal portion 35 of bone plate 30 is attached to bone portion 102, for instance, by insertion of one or more fasteners, such as fastener 16h, through one or more of the openings, such as 16h, present in the distal portion 35 of the secondary plate 30.

The primary bone plate 20 is positioned along a first bone portion 102, such as a long or diaphyseal bone portion of bone 100. For example, as depicted, the primary bone plate is positioned along the proximal radial portion of the distal radius. Fastener 16a is inserted into opening 15a thereby attaching the bone plate 20 to the first portion of bone 102.

The primary and secondary bone plates 20 and 30 are appropriately positioned and the bone plate engagement elements 19a and 19b of the primary and secondary bone plates are aligned, coupled, and attached e.g., via fastener 16b, so as to reduce the two bone portions 102 and 104 and thereby stabilize the fractured bone portions.

As illustrated, the configuration of the primary and secondary bone plates is adapted so as to model the morphology of the bone regions to which the primary and secondary bone plates are attached. Therefore, the bottom surface 31 of the secondary bone plate 30 is curved and/or angled, and the bottom surface of the primary bone plate 20 is substantially planar. Accordingly, as can be seen with reference to FIG. 6B, the bone contacting surface 31 of the secondary bone plate 30 substantially corresponds to a secondary plane 2, which secondary plane 2 transects the primary plane 1 at an angle x.

Figure 7A:
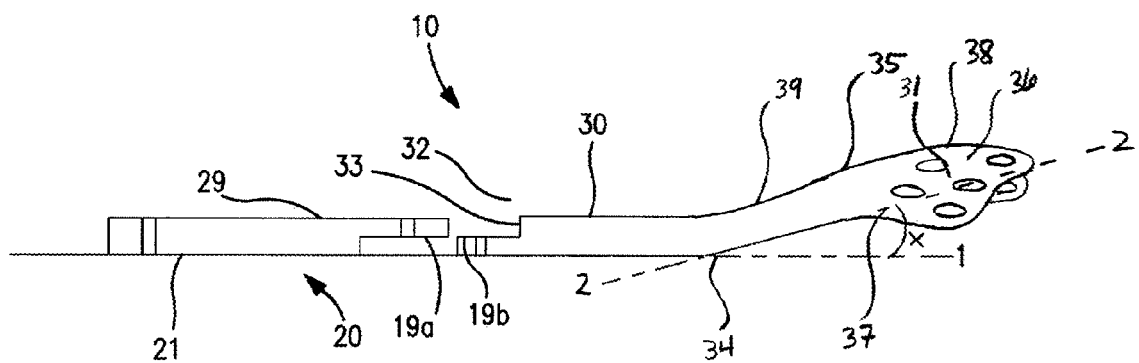
FIG. 7A provides a side view of a bone plate system as described herein, wherein the secondary bone plate is angled and concave.

FIG. 7 illustrates another variation of the bone plate system of the disclosure. As can be seen with respect to FIG. 7A, the bone plate system includes a primary bone plate 20. The primary bone plate 20 is planar, includes a top surface 29 with a primary bone plate engagement element 19a, configured as a cut out-tab receiving element, and additionally includes a bone contacting surface 21, which surface defines a primary plane 1.

The bone plate system further includes a secondary bone plate 30. The secondary bone plate 30 is non-planar and includes a proximal portion 32, with a proximal end 33, an intercalating portion 34, and a distal portion 35 with a distal end 36. Bone plate 30 additionally includes a top surface 39, a bone contacting surface 31, and further includes a primary bone plate engagement element 19b configured as a tab insertion member. The proximal 32 and distal 35 portions of the secondary bone plate are angled with respect to each other. Specifically, the bone contacting surface 31 of the distal portion 35 of the secondary bone plate 30 defines a secondary plane 2, which plane transects the primary plane 1, at an angle x. Accordingly, the proximal portion 32 is angled with respect to the distal portion 35, wherein the angle x may range from about 1° to about 90°, such as from about 5° to about 45°, for instance, from about 7.5° to about 30°, including from about 10° to about 20°, such about as 15°.

Additionally, as depicted, the bone contacting surface 31 in the distal portion 35 of the secondary bone plate 30 includes a curvature between sides 37 and 38 such that the distal portion 35 of the bone plate 30 is concave, which concavity is dimensioned so as to snugly fit the curvature of a bone portion. Specifically, in certain embodiments, the first 37 and second 38 sides of the secondary bone plate 30 may include a curvature there between, e.g., the bone contacting surface 31 may be curved between sides 37 and 38, which curvature may span a portion or the entire length of the secondary bone plate.

Figure 7B:
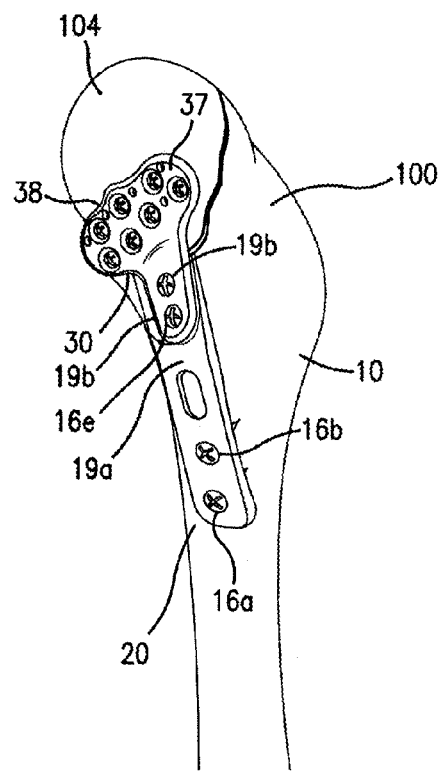
FIG. 7B provides a perspective view of the bone plate system of FIG. 7A, wherein the primary and secondary bone plates are attached to respective bone portions and coupled together.

For instance, the curvature may span the entire length of the bone contacting surface 31, or the curvature may span only a distal 35 or proximal portion 32. For example, the sides 37 and 38 of a distal portion 35 may have a curvature there between, whereas the sides 37 and 38 of proximal portion 32 do not have a curvature there between and thus the bone contacting surface 31 of the proximal portion 32 is relatively planar, and the bone contacting surface 31 of the distal portion 35, between sides 37 and 38, is not planar but curved. In certain embodiments, the degree of curvature ranges from about 2.78 mm radius of curvature to about 13 mm radius. In certain embodiments, the curvature of the secondary bone plate 30 is configured so as to wrap around a curved bone structure as depicted in FIG. 7B, so as to snugly fit the bone portion. In certain embodiments, although not shown, the entire primary bone plate or a portion thereof may as well have a corresponding curvature, as described above.

As can be seen with reference to FIG. 7B, a periarticualr radial bone portion 104 of the radius bone 100 may be fractured and dislocated from a diaphyseal portion 102 of the bone 100. Accordingly, the primary bone plate 20 may be positioned along a first bone portion 102. As depicted, bone plate 20 is attached to a radial surface 102 of the radius bone 100. Bone plate 20 is attached proximally to the fracture site.

Fasteners 16a and 16b are inserted into an opening in the primary bone plate 20 thereby attaching the bone plate 20 to the first portion of bone 102.

Likewise, the secondary bone plate 30 is positioned along a second bone portion 104, such as a displaced radial styloid bone portion, and fasteners 16i and j are inserted into openings in the secondary bone plate 30 thereby attaching the bone plate 30 to the second portion of bone 104. As depicted, bone plate 30 is positioned on the most distal fragment of the distal radius securing the bone proximal to the articular surface. Hence, bone plate 30 is positioned on the radial surface of the distal radius fragment.

As illustrated, the configuration of the secondary bone plate 30 is adapted so as to model the morphology of the bone region to which the secondary bone plate is attached, and the tab portion 19b is configured such that when the bone portion 104 is properly aligned with respect to bone portion 102, tab portion 19b of the secondary bone plate 30 may be fit within the tab receiving portion 19a of the primary bone plate 20 so as to properly reduce and stabilize the fractured bone portions 102 and 104.

Once the primary and secondary bone plates 20 and 30 are appropriately positioned, the bone plate engagement elements 19a and 19b of the primary and secondary bone plates 20 and 30 may be coupled and attached to one another via the insertion of fastener 16e. In this manner the two bone portions 102 and 104 may be reduced to a position that approximates the position they were in prior to the bone fracture and thereby stabilize the fractured bone portions.

Accordingly, the bone plate system 10 of the present disclosure is configured for engaging the dislocated portions such that by attachment of the primary and secondary bone plates 20 and 30 to respective bone portions 102 and 104 and alignment, coupling, and attachment of the plates with one another, the fractured bone portions may be properly reduced and stabilized. When bone plate 20 and bone plate 30 are secured together the fracture is properly reduced such that the articular surface of the distal radius is in its anatomical position. For example, this should approximate the position prior to the bone fracture. This is in a position of an approximate volar angulation of about 12° and an ulnar inclination of about 22°.

In one aspect, the subject matter described herein is directed to methods of using such bone plate systems, as described herein above, so as to align, reduce and/or fix one or more fractured bone portions for the treatment thereof, for example. Accordingly, in certain embodiments, a general method is provided for reducing a bone fracture, wherein the method includes the steps of providing a first and a second bone plate, wherein the first and second bone plates are configured for being coupled to one another in an angled relationship, attaching the first bone plate to a first bone portion, attaching the second bone plate to a second bone portion, and coupling the first and second bone plates together so as to reduce the fractured bone portions.

The bone plates may be attached to their respective bone portions in any suitable order. For instance, the secondary bone plate may be attached to a second bone portion prior to the attachment of the primary bone plate to a first bone portion or vice-verse. However, regardless of the order of the attachment of the primary and secondary plates, the secondary bone plate may be attached to a distal and/or fragmented bone portion and used as a lever so as to obtain correct anatomical alignment.

For example, the secondary bone plate may first be applied to a distal bone fragment. The application of the secondary bone plate to the distal bone fragment may, but need not, involve the use of a K-wire which may be inserted through an opening in the secondary bone plate, for instance, in the distal portion thereof, so as to be used as a guide to insure correct alignment of the secondary bone plate to the distal fractured bone portion. Accordingly, the K-wire to be applied may be drilled parallel to an articular surface, such as in the lateral plane of the bone fragment. The secondary plate may then be slid over the K-wire and down to the surface of the distal bone fragment. Once contacted and correctly positioned with respect to the distal bone fragment, the secondary bone plate may be attached thereto by the insertion of one or more fasteners, e.g., pegs, through openings in the secondary bone plate. K-wire may also be used to perform this function in addition or substitution for the referenced pegs.

If the primary plate has not heretofore been attached to the primary bone portion it may then be attached to its respective bone portion, for instance, in the manner described above with respect to the secondary bone plate. Once the secondary bone plate or both the primary and secondary bone plates are attached to their respective bone portions, the secondary bone plate may be used, like a joystick, so as to align the two bone portions together and reduce the fracture and/or align the bone plate engagement element of the secondary bone plate, with the bone plate engagement element of the primary bone plate in a manner sufficient to allow the primary and secondary bone plates to be coupled together. It is to be noted that the primary and secondary bone plates are not only specifically designed, as described above, to conform to the morphology of the bone portions to which they are attached, but are also designed such that when the primary and secondary bone plates are attached to their respective bone portions, the coupling of the primary and secondary bone plates to one another results in the alignment and proper reduction of the respective bone portions such that when the primary and secondary bone plates are attached to one another the fractured bone portions are stabilized in an alignment that approximates the normal anatomical alignment that the bone was in prior to the fracture and therefore promotes correct and rapid healing, with minimal adverse effects.

In one aspect, the disclosure is directed to a kit, wherein the kit includes a plurality of bone plates. In certain variations the kit includes a plurality of bone plates including a primary bone plate, a secondary bone plate, and/or a fastener of the disclosure. For instance, in certain variations, the kit includes at least a primary bone plate and a secondary bone plate, as described above, and may additionally include one or more fasteners. In certain variations the kit includes a plurality of primary and secondary bone plates and a plurality of fasteners. For example, in certain variations, a kit is provided wherein the kit includes at least a plurality of primary and secondary bone plates which bone plates may be configured such that they may be bent, manipulated, mixed, matched, and attached to one or more bone portions and/or to each other so as to reduce, align, and stabilize a bone fracture through the use of a multiplicity of bone plates. The kit may also include suitable directions for using the components of the kit. Such as directions pertaining to mixing and matching the components, so as to optimize usability.

As certain changes may be made without departing from the scope of the present subject matter described herein, it is intended that all matter contained in the above description or shown in the accompanying drawings be interpreted as illustrative and not in a literal sense (and thus, not limiting). Practitioners of the art will realize that the method, device and system configurations depicted and described herein are examples of multiple possible system configurations that fall within the scope of the current subject matter described herein.

While the subject matter described herein has been described with reference to the specific embodiments thereof, it should be understood by those skilled in the art that various changes may be made and equivalents may be substituted without departing from the true spirit and scope of the subject matter described herein. In addition, many modifications may be made to adapt a particular situation, material, composition of matter, process, process step or steps, to the objective and scope of the subject matter described herein. All such modifications are intended to be within the scope of the claims appended hereto.

Throughout this application, various publications, patents and published patent applications may be cited. The disclosures of these publications, patents and published patent applications referenced in this application are hereby incorporated by reference in their entirety into the present disclosure. Citation herein by the Applicant of a publication, published patent application, or patent is not an admission by the Applicant of said publication, published patent application, or patent as prior art. Accordingly, all publications and patents cited in this specification are herein incorporated by reference as if each individual publication or patent were specifically and individually indicated to be incorporated by reference.

What is claimed is:

1. A bone plate system, comprising:
    a substantially elongate primary bone plate that extends along an axis, comprising:
        a primary bone plate bone contacting surface;
        a primary bone plate top surface opposite to the bone contacting surface;
        a plurality of openings extending between the primary bone plate bone contacting surface and the primary bone plate top surface, at least one of the openings being configured to receive a fastener to attach the primary bone plate to a first portion of bone; and
        at least one of the primary bone plate bone contacting surface and the primary bone plate top surface substantially corresponding to a primary plane; and
    a secondary bone plate for engagement with the primary bone plate comprising:
        a portion configured for engaging one or more of a second portion of the bone and the primary bone plate; and
        a secondary bone plate bone contacting surface, wherein:
        the secondary bone plate bone contacting surface corresponds to one or more planes or an arc which are provided at an angle or substantially perpendicular to the primary plane,
        the primary bone plate including a first engagement element that engages a second engagement element of the secondary bone plate to connect the primary and secondary bone plates while allowing for relative angular movement between the engagement elements of the bone plates within the primary plane and in a direction that is transverse to the axis of the primary bone plate,
        the first engagement element including a first opening and a second opening, the first opening for receiving a fastener to connect the secondary bone plate to the primary bone plate, the second opening extending transverse to the axis of the primary bone plate and receiving a fastener to fix the angular position of the primary bone plate relative to the secondary bone plate, the first opening being circular, the second opening having an arc or ovoid shape and being distal of the first opening.

2. The bone plate system according to claim 1, wherein the primary bone plate comprises a diaphyseal bone plate.

3. The bone plate system according to claim 1, wherein the secondary bone plate comprises a periarticular bone plate.

4. The bone plate system according to claim 1, wherein the primary plane corresponds to the primary bone plate bone contacting surface.

5. The bone plate system according to claim 1, wherein the primary plane corresponds to the primary bone plate top surface.

6. The bone plate system according to claim 1, wherein the angle is from about 1° to about 90°.

7. The bone plate system according to claim 6, wherein the angle is selected from the group consisting of about 1°, about 5°, about 7.5°, about 10°, and about 15°.

8. The bone plate system according to claim 1, wherein the bone contacting surface of the secondary bone plate comprises an arc.

9. The bone plate system according to claim 8, wherein the arc has a radius of curvature that is selected from the group consisting of a constant, decreasing, and increasing radius of curvature.

10. The bone plate system according to claim 1, wherein the primary bone plate comprises a distal portion, a distal end, an intercalating portion, proximal portion, and a proximal end.

11. The bone plate system according to claim 10, wherein the bone contacting surface of the primary bone plate comprises a first side and a second side, and the bone contacting surface further comprises a curvature between the first and second sides.

12. The bone plate system according to claim 11, wherein the distal portion comprises the curvature and the proximal portion is substantially planar.

13. The bone plate system according to claim 11, wherein the proximal portion comprises the curvature and the distal portion is substantially planar.

14. The bone plate system according to claim 1, wherein at least one of the openings of the primary bone plate is positioned in a proximal portion of the primary bone plate.

15. The bone plate system according to claim 14, wherein the opening comprises an arced or ovoid aperture.

16. The bone plate system according to claim 10, wherein the distal portion of the primary bone plate includes the first engagement element configured for engaging the secondary bone plate.

17. The bone plate system according to claim 16, wherein the second engagement element is angled with respect to the distal portion of the primary bone plate.

18. The bone plate system according to claim 10, wherein the intercalating portion is configured for being extended and/or contracted.

19. The bone plate system according to claim 10, wherein a proximal portion of the secondary bone plate further comprises the second engagement element configured for engaging the primary bone plate, wherein the second engagement element is angled with respect to a distal portion of the primary bone plate.

20. The bone plate system according to claim 1, wherein the first engagement element includes a tapered recess and the second engagement element includes a tab, the tab moving within the primary plane and transverse to the axis of the primary bone plate while the tab is within the tapered recess in order to adjust the angular position of the secondary bone plate relative to the primary bone plate.

21. A bone plate system comprising:
a primary bone plate that extends along an axis from a proximal end to a distal end, at least one opening extending through the proximal end and being configured to receive a fastener to attach the primary bone plate to a first portion of bone, the primary bone plate extending within a primary plane; and
a secondary bone plate for engagement with the primary bone plate, the secondary bone plate extending from a proximal end to a distal end, at least one opening extending through the distal end of the secondary bone plate and being configured to receive a fastener to attach the secondary bone plate to a second portion of the bone,
wherein the distal end of the primary bone plate includes a first engagement element that engages a second engagement element on the proximal end of the secondary bone plate to connect the primary and secondary bone plates while allowing for relative angular movement between the engagement elements of the bone plates within the primary plane and in a direction that is transverse to the axis of the primary bone plate,
wherein the first engagement element includes a pair of sidewalls on opposite sides of the axis of the primary bone plate and extending towards the bone, the second engagement element including a pair of sides on opposite sides of the at least one opening in the secondary bone plate that are positioned between the sidewalls of the first engagement element when the primary bone plate and secondary bone plate are connected together.

22. The bone plate system according to claim 21, wherein the primary bone plate further includes an elongated opening for receiving a fastener to fix the secondary bone plate to the primary bone plate at any one of a plurality of angular positions relative to the primary bone plate.

23. The bone plate system according to claim 21, wherein the first engagement element includes a tapered recess and the second engagement element includes a tab, the tab moving within the primary plane and transverse to the axis of the primary bone plate while the tab is within the tapered recess in order to adjust the angular position of the secondary bone plate relative to the primary bone plate.

24. The bone plate system according to claim 1, wherein the second engagement element resides in the primary plane, the engagement elements being capable of planar, angular movement relative to one another within the primary plane while the primary and secondary bone plates are connected to one another.

25. The bone plate system according to claim 1, wherein the first engagement element is integrally formed with and fixed to the primary bone plate and the second engagement element is integrally formed with and fixed to the secondary bone plate.

26. The bone plate system according to claim 21, wherein the second engagement element resides in the primary plane, the engagement elements being capable of planar, angular movement relative to one another within the primary plane while the primary and secondary bone plates are connected to one another.

27. The bone plate system according to claim 21, wherein the first engagement element includes a first opening and a second opening, the first opening for receiving a fastener to connect the secondary bone plate to the primary bone plate, the second opening for receiving a fastener to fix the angular position of the primary bone plate relative to the secondary bone plate.

28. The bone plate system according to claim 27, wherein the first engagement element is integrally formed with and fixed to the primary bone plate and the second engagement element is integrally formed with and fixed to the secondary bone plate.

* * * * *